US011434272B2

(12) United States Patent
Hinrichs et al.

(10) Patent No.: US 11,434,272 B2
(45) Date of Patent: *Sep. 6, 2022

(54) ANTI-HUMAN PAPILLOMAVIRUS 16 E7 T CELL RECEPTORS

(71) Applicant: The United States of America, as represented by the Secretary, Department of Health and Human Services, Bethesda, MD (US)

(72) Inventors: Christian S. Hinrichs, Bethesda, MD (US); Steven A. Rosenberg, Potomac, MD (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 17/101,360

(22) Filed: Nov. 23, 2020

(65) Prior Publication Data

US 2021/0130432 A1 May 6, 2021

Related U.S. Application Data

(60) Continuation of application No. 16/205,631, filed on Nov. 30, 2018, now Pat. No. 10,870,687, which is a division of application No. 15/313,673, filed as application No. PCT/US2015/033129 on May 29, 2015, now Pat. No. 10,174,098.

(60) Provisional application No. 62/004,335, filed on May 29, 2014.

(51) Int. Cl.
| *A61K 38/17* | (2006.01) |
| *A61K 48/00* | (2006.01) |
| *C07K 14/725* | (2006.01) |
| *G01N 33/569* | (2006.01) |
| *C07K 16/28* | (2006.01) |
| *G01N 33/574* | (2006.01) |
| *A61K 38/00* | (2006.01) |

(52) U.S. Cl.
CPC ...... *C07K 14/7051* (2013.01); *A61K 38/1774* (2013.01); *C07K 16/2809* (2013.01); *G01N 33/56983* (2013.01); *G01N 33/57484* (2013.01); *A61K 38/00* (2013.01); *C07K 2319/00* (2013.01); *C07K 2319/32* (2013.01); *G01N 2333/025* (2013.01)

(58) Field of Classification Search
CPC . C07K 7/06; C07K 7/08; C07K 14/47; C07K 14/705; C07K 14/7051; C07K 2319/32; C07K 2319/33; A61K 38/08; A61K 38/10; A61K 38/177; A61K 38/1774
See application file for complete search history.

(56) References Cited

U.S. PATENT DOCUMENTS

| 5,087,616 A | 2/1992 | Myers et al. |
| 5,225,539 A | 7/1993 | Winter |
| 5,449,752 A | 9/1995 | Fujii et al. |
| 5,545,806 A | 8/1996 | Lonberg et al. |
| 5,569,825 A | 10/1996 | Lonberg et al. |
| 5,585,089 A | 12/1996 | Queen et al. |
| 5,639,641 A | 6/1997 | Pedersen et al. |
| 5,693,761 A | 12/1997 | Queen et al. |
| 5,714,352 A | 2/1998 | Jakobobits et al. |
| 6,265,150 B1 | 7/2001 | Terstappen et al. |
| 8,034,334 B2 | 10/2011 | Dudley et al. |
| 8,383,099 B2 | 2/2013 | Dudley et al. |
| 10,174,098 B2 | 1/2019 | Hinrichs et al. |
| 10,870,687 B2 * | 12/2020 | Hinrichs ............... A61P 1/00 |
| 2002/0197266 A1 | 12/2002 | Debinski |
| 2010/0189742 A1 | 7/2010 | Van Der Burg et al. |
| 2012/0244133 A1 | 9/2012 | Rosenberg et al. |

FOREIGN PATENT DOCUMENTS

| EP | 0239400 B1 | 8/1994 |
| GB | 2188638 A | 10/1987 |
| JP | 2013-505734 A | 2/2013 |
| WO | WO 2006/103429 A2 | 10/2006 |
| WO | WO 2007/131092 A2 | 11/2007 |

(Continued)

OTHER PUBLICATIONS

Choi et al., "Synthesis and Assembly of a Cholera Toxin B Subunit-Rotavirus VP7 Fusion Protein in Transgenic Potato," Mol. Biotechnol., 31: 193-202 (2005).
Cohen et al., "Enhanced Antitumor Activity of T Cells Engineered to Express T-Cell Receptors with a Second Disulfide Bond," *Cancer Res.*, 67(8): 3898-903 (2007).
Dudley et al., "Generation of Tumor-Infiltrating Lymphocyte Cultures for Use in Adoptive Transfer Therapy for Melanoma Patients," *J. Immunother.*, 26:332-42 (2003).
European Patent Office, Extended European Search Report in European Application No. 19217074.4, dated Jul. 2, 2020.
Ferradini et al., "Studies on the human T cell receptor alpha/beta variable region genes, Part II," *Eur. J. Immunol.*, 21: 935-942 (1991).
Haga-Friedman et al., "Incorporation of Transmembrane Hydrophobic Mutations in the TCR Enhance Its Surface Expression and T Cell Functional Avidity," *J. Immunol.*, 188: 5538-5546 (2012).

(Continued)

*Primary Examiner* — Jeffrey E. Russel
(74) *Attorney, Agent, or Firm* — Leydig, Voit & Mayer

(57) ABSTRACT

Disclosed is a synthetic T cell receptor (TCR) having antigenic specificity for an HLA-A2-restricted epitope of human papillomavirus (HPV) 16 E7, $E7_{11-19}$. Related polypeptides and proteins, as well as related nucleic acids, recombinant expression vectors, host cells, and populations of cells are also provided. Antibodies, or an antigen binding portion thereof, and pharmaceutical compositions relating to the TCRs of the invention are also provided. Also disclosed are methods of detecting the presence of a condition in a mammal and methods of treating or preventing a condition in a mammal, wherein the condition is cancer, HPV 16 infection, or HPV-positive premalignancy.

20 Claims, 9 Drawing Sheets

Specification includes a Sequence Listing.

(56) References Cited

FOREIGN PATENT DOCUMENTS

| WO | WO 2011/039508 A2 | 4/2011 |
|---|---|---|
| WO | WO 2015/009606 A1 | 1/2015 |

OTHER PUBLICATIONS

Haskard et al, "The Production of Human Monoclonal Autoantibodies from Patients with Rheumatoid Arthritis by the EBV-Hybridoma Technique," *J. Immunol. Methods*, 74(2), 361-67 (1984).
Hinrichs et al., "HPV-targeted tumor-infiltrating lymphocytes for cervical cancer," Abstract, ASCO Annual Meeting May 14, 2014.
Hudecz "Synthesis of Peptide Bioconjugates," *Methods Mol. Biol.*, 298: 209-223 (2005).
Huse et al., "Generation of a Large Combinatorial Library of the Immunoglobulin Repertoire in Phage Lambda," *Science*, 246: 1275-81 (1989).
International Bureau, International Search Report in International Patent Application No. PCT/US2015/033129, dated Aug. 27, 2015.
International Bureau, Written Opinion in International Patent Application No. PCT/US2015/033129, dated Aug. 27, 2015.
Keskin et al., "Direct identification of an HPV-16 tumor antigen from cervical cancer biopsy specimens," *Frontiers in Immunology*, 2 (2011).
Kirin et al., "Amino Acid and Peptide Bioconjugates of Copper(II) and Zinc(II) Complexes with a Modified *N,N*-Bis(2-picolyl)amine Ligand," *Inorg Chem.*, 44(15):5405-5415 (2005).
Köhler et al., "Derivation of specific antibody-producing tissue culture and tumor lines by cell fusion," *Eur. J. Immunol.*, 5: 511-519 (1976).
Lyons et al., "T-cell receptor tetramer binding or the lack there of does not necessitate antigen reactivity in T-cell receptor transduced T cells," *Cancer Immunol. Immunother.*, 55(9): 1142-50 (2006).
Meydan et al., "Prediction of peptides binding to MHC class I and II alleles by temporal motif mining," *BMC Bioinformatics*, 14(Suppl 2):S13 (2013).
Nilges et al., "Human Papillomavirus Type 16 E7 Peptide-Directed CD8+ T Cells from Patients with Cervical Cancer are Cross-Reactive with the Coronavirus NS2 Protein," *J. Virol.*, 77(9): 5464-74 (2003).

Pedersen et al., "Comparison of Surface Accessible Residues in Human and Murine Immunoglobulin Fv Domains: Implication for Humanization of Munrine Antibodies," *J. Mol. Biol.*, 235: 959-973 (1994).
Reiter et al., "Engineering interchain disulfide bonds into conserved framework regions of Fv fragments: improved biochemical characteristics of recombinant immunotoxins containing disulfide-stabilized Fv," *Protein Engineering*, 7: 697-704 (1994).
Riddell et al., "The use of anti-CD3 and anti-CD28 monoclonal antibodies to clone and expand human antigen-specific T cells," *J. Immunol. Methods*, 128:189-201 (1990).
Riemer et al., "A Conserved E7-derived Cytotoxic T Lymphocyte Epitope Expressed on Human Papillomavirus 16-transformed HLA-A2 + Epithelial Cancers," *Journal of Biological Chemistry*, 285(38): 29608-29622 (2010).
Roder et al., "The EBV-Hybridoma Technique," *Methods Enzymol.*, 121: 140-67 (1986).
Roman-Roman et al., "Studies on the human T cell receptor alpha/beta variable region genes, Part I," *Eur. J. Immunol.*, 21: 935-942 (1991).
Scholten et al., "Preservation and redirection of HPV16E7-specific T cell receptors for immunotherapy of cervical cancer," *Clinical Immunology*, 114(2): 119-129 (2005).
Scholten et al., "Promiscuous behavior of HPV16E6 specific T cell expression in TCR transgenic T cells, which can be restored in part by genetic modification," *Cellular Oncology*, 32(1-2): 43-56 (2010).
Scholten et al., "Generating HPV specific T helper cells for the treatment of HPV induced malignancies using TCR gene transfer," *J. Transl. Med.*, 9: 147 (2011).
"TRA T-cell receptor alpha locus [*Homo sapiens* (human)]," Gene ID: 6955, (updated Oct. 9, 2016), Entrez Gene (ncbi.nlm.nih.gov/gene), printed on Dec. 8, 2016.
"TRB T cell receptor beta locus [*Homo sapiens* (human)]," Gene ID: 6957, (updated Oct. 9, 2016), Entrez Gene (ncbi.nlm.nih.gov/gene), printed on Dec. 8, 2016.
Wadwa et al., "Receptor Mediated Glycotargeting," *J. Drug Targeting*, 3: 111 (1995).
Youde et al., "Cross-typic specificity and immunotherapeutic potential of a human HPV16 E7-specific CTL line," *International Journal of Cancer*, 114(4): 606-612 (2005).

* cited by examiner

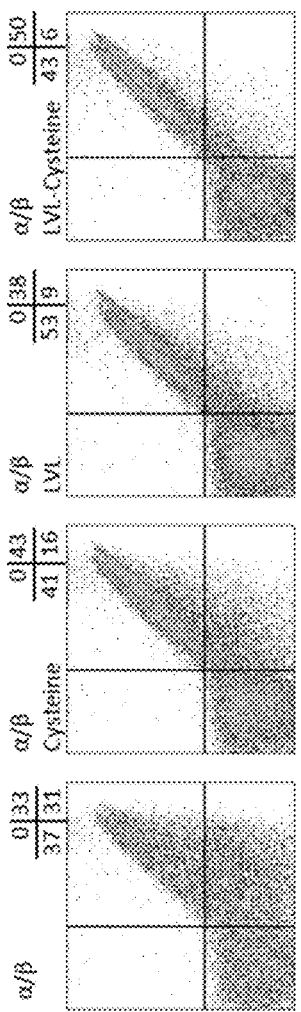
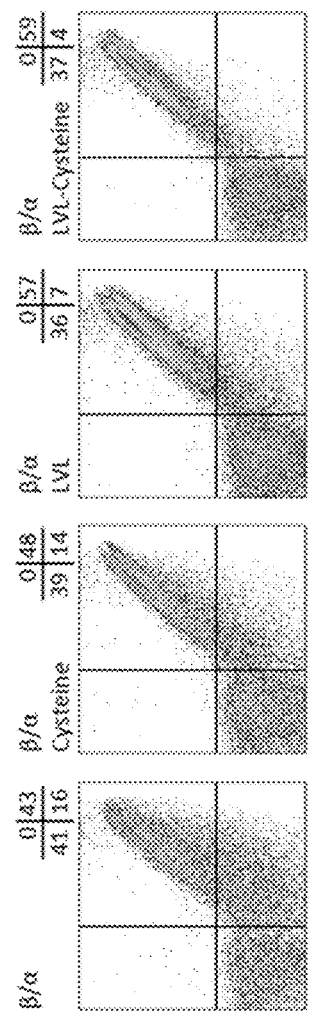
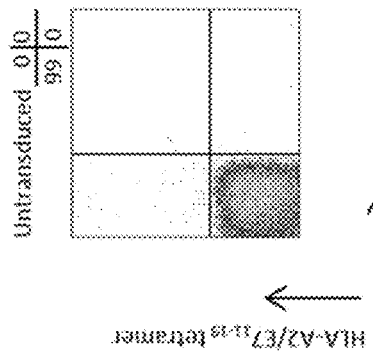

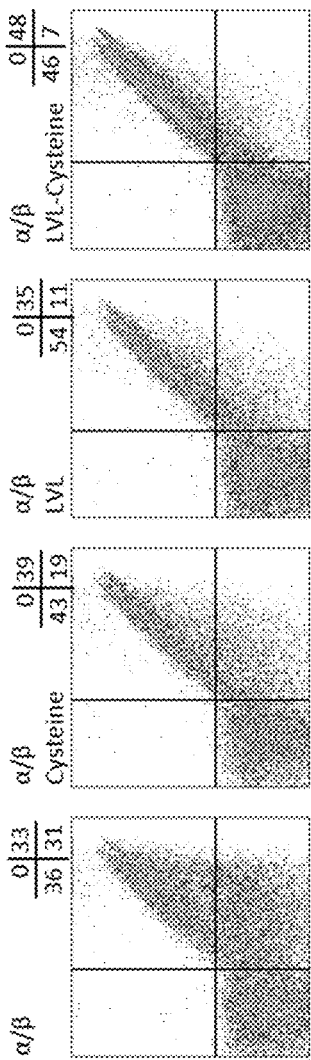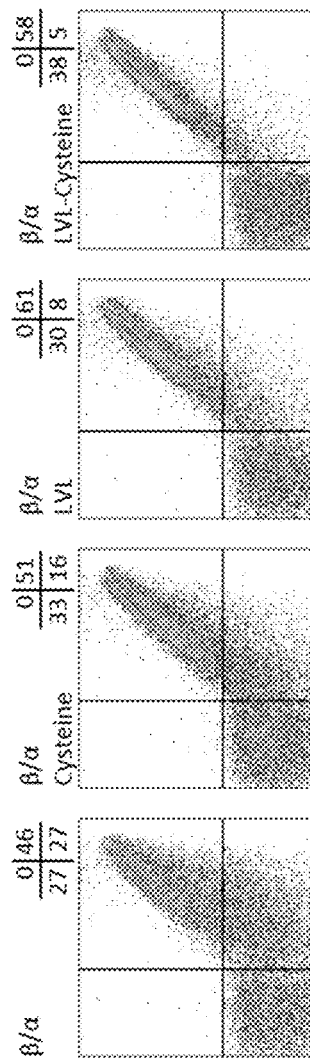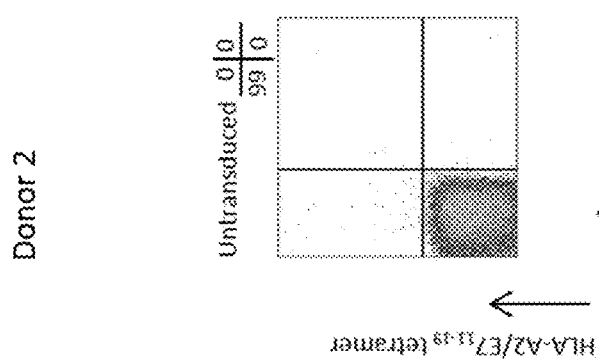

ANTI-HUMAN PAPILLOMAVIRUS 16 E7 T CELL RECEPTORS

CROSS-REFERENCE TO RELATED APPLICATION

This patent application is a continuation of U.S. application Ser. No. 16/205,631, filed Nov. 30, 2018, which is a divisional of U.S. application Ser. No. 15/313,673, now U.S. Pat. No. 10,174,098, which is the U.S. national stage of PCT/US2015/033129, filed May 29, 2015, which claims the benefit of U.S. Provisional Patent Application No. 62/004,335, filed May 29, 2014, each of which is incorporated by reference in its entirety herein.

STATEMENT REGARDING FEDERALLY SPONSORED RESEARCH AND DEVELOPMENT

This invention was made with Government support under project numbers ZIABC010984-5 and ZIABC011479 by the National Institutes of Health, National Cancer Institute. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 78,742 Byte ASCII (Text) file named "751002_ST25.TXT" dated Nov. 11, 2020.

BACKGROUND OF THE INVENTION

The primary cause of some cancer types such as, for example, uterine cervical cancer, is human papillomavirus (HPV) infection. Despite advances in treatments such as chemotherapy, the prognosis for many cancers, including HPV-associated cancers, may be poor. Accordingly, there exists an unmet need for additional treatments for cancer, particularly HPV-associated cancers.

BRIEF SUMMARY OF THE INVENTION

An embodiment of the invention provides an isolated or purified T cell receptor (TCR) having antigenic specificity for human papillomavirus (HPV) 16 E7.

Another embodiment of the invention provides a TCR comprising a human variable region and a murine constant region, or a functional variant of the TCR, wherein the TCR and the functional variant have antigenic specificity for human papillomavirus (HPV) 16 E7.

The invention further provides related polypeptides and proteins, as well as related nucleic acids, recombinant expression vectors, host cells, and populations of cells. Further provided by the invention are antibodies, or antigen binding portions thereof, and pharmaceutical compositions relating to the TCRs (including functional portions and functional variants thereof) of the invention.

Methods of detecting the presence of a condition in a mammal and methods of treating or preventing a condition in a mammal, wherein the condition is cancer, HPV 16 infection, or HPV-positive premalignancy, are further provided by the invention. The inventive method of detecting the presence of a condition in a mammal comprises (i) contacting a sample comprising cells of the condition with any of the inventive TCRs (including functional portions and functional variants thereof), polypeptides, proteins, nucleic acids, recombinant expression vectors, host cells, populations of host cells, antibodies, or antigen binding portions thereof, or pharmaceutical compositions described herein, thereby forming a complex, and (ii) detecting the complex, wherein detection of the complex is indicative of the presence of the condition in the mammal, wherein the condition is cancer, HPV 16 infection, or HPV-positive premalignancy.

The inventive method of treating or preventing a condition in a mammal comprises administering to the mammal any of the TCRs (including functional portions and functional variants thereof), polypeptides, or proteins described herein, any nucleic acid or recombinant expression vector comprising a nucleotide sequence encoding any of the TCRs (including functional portions and functional variants thereof), polypeptides, proteins described herein, or any host cell or population of host cells comprising a recombinant vector which encodes any of the TCRs (including functional portions and functional variants thereof), polypeptides, or proteins described herein, in an amount effective to treat or prevent the condition in the mammal, wherein the condition is cancer, HPV 16 infection, or HPV-positive premalignancy.

BRIEF DESCRIPTION OF THE SEVERAL VIEWS OF THE DRAWINGS

FIGS. 2A-2R are dot plots showing the percentage of cells from a first donor (A-I) or a second donor (J-R) that were transduced (B-I and K-R) with one of the recombinant expression vectors set forth in Table 1 which expressed the following: HLA-A2/$E7_{11-19}$ tetramer$^+$/m TRBC$^-$ (upper left quadrant), HLA-A2/$E7_{11-19}$ tetramer$^+$/m TRBC$^+$ (upper right quadrant), HLA-A2/$E7_{11-19}$ tetramer$^-$/m TRBC$^-$ (lower left quadrant), and HLA-A2/$E7_{11-19}$ tetramer$^-$/m TRBC$^+$ (lower right quadrant). The numerical percentages for each quadrant are provided above each dot plot. Untransduced cells (A and J) were used as a negative control.

DETAILED DESCRIPTION OF THE INVENTION

Figure 1:
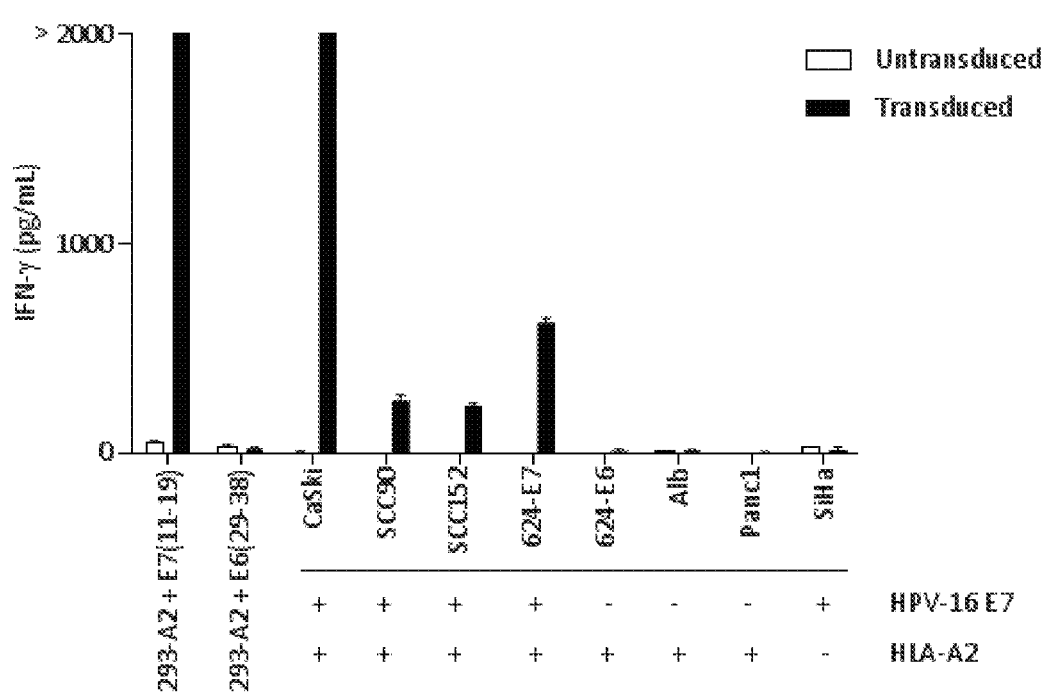
FIG. 1 is a bar graph showing interferon (IFN)-γ (pg/mL) secreted by peripheral blood lymphocytes (PBL) that were transduced with a nucleotide sequence encoding a chimeric anti-HPV 16 E7 TCR (shaded bars) upon co-culture with target 293-A2 cells pulsed with HPV 16 $E6_{29-38}$ peptide, 293-A2 cells pulsed with HPV 16 $E7_{11-19}$ peptide, 624 cells transduced with a plasmid encoding HPV 16 E6, 624 cells transduced with a plasmid encoding HPV 16 E7, SCC152 cells, SCC90 cells, CaSki cells, Alb cells, Pancl cells, or SiHa cells. HLA-A2 and HPV-16 E7 expression by each target cell is indicated in the bottom of FIG. 1 ("+" indicates positive for expression and "−" indicates negative for expression). Untransduced cells (unshaded bars) were used as a negative control.

An embodiment of the invention provides an isolated or purified T cell receptor (TCR) having antigenic specificity for human papillomavirus (HPV) 16 E7.

HPV 16 is the subtype of HPV that is most commonly associated with malignancy. Without being bound to a particular theory or mechanism, HPV 16 is believed to cause cancer at least partly through the actions of the oncoprotein E7, which keeps cancer cells active in the cell division cycle through Rb inactivation. HPV 16 E7 is constitutively expressed in cancer cells and is not expressed by normal, uninfected human tissues. HPV 16 E7 is expressed in a variety of human cancers including, but not limited to, cancer of the uterine cervix, oropharynx, anus, anal canal, anorectum, vagina, vulva, and penis.

The inventive TCR (including functional portions and functional variants thereof) may have antigenic specificity for any HPV 16 E7 protein, polypeptide or peptide. In an embodiment of the invention, the TCR (including functional portions and functional variants thereof) has antigenic specificity for a HPV 16 E7 protein comprising, consisting of, or consisting essentially of, SEQ ID NO: 1. In a preferred embodiment of the invention, the TCR (including functional portions and functional variants thereof) has antigenic specificity for a HPV 16 E7$_{11\text{-}19}$ peptide comprising, consisting of, or consisting essentially of, YMLDLQPET (SEQ ID NO: 2).

In an embodiment of the invention, the inventive TCRs (including functional portions and functional variants thereof) are able to recognize HPV 16 E7 in a major histocompatibility complex (MHC) class I-dependent manner. "MHC class I-dependent manner," as used herein, means that the TCR (including functional portions and functional variants thereof) elicits an immune response upon binding to HPV 16 E7 within the context of an MHC class I molecule. The MHC class I molecule can be any MHC class I molecule known in the art, e.g., HLA-A molecules. In a preferred embodiment of the invention, the MHC class I molecule is an HLA-A2 molecule.

The TCRs (including functional portions and functional variants thereof) of the invention provide many advantages, including when expressed by cells used for adoptive cell transfer. Without being bound by a particular theory or mechanism, it is believed that because HPV 16 E7 is expressed by HPV 16-infected cells of multiple cancer types, the inventive TCRs (including functional portions and functional variants thereof) advantageously provide the ability to destroy cells of multiple types of HPV 16-associated cancer and, accordingly, treat or prevent multiple types of HPV 16-associated cancer. Additionally, without being bound to a particular theory or mechanism, it is believed that because the HPV 16 E7 protein is expressed only in cancer cells, the inventive TCRs (including functional portions and functional variants thereof) advantageously target the destruction of cancer cells while minimizing or eliminating the destruction of normal, non-cancerous cells, thereby reducing, for example, by minimizing or eliminating, toxicity. Moreover, the inventive TCRs (including functional portions and functional variants thereof) may, advantageously, successfully treat or prevent HPV-positive cancers that do not respond to other types of treatment such as, for example, chemotherapy alone, surgery, or radiation. Additionally, the inventive TCRs (including functional portions and functional variants thereof) provide highly avid recognition of HPV 16 E7, which may, advantageously, provide the ability to recognize unmanipulated tumor cells (e.g., tumor cells that have not been treated with interferon (IFN)-γ, transfected with a vector encoding one or both of HPV 16 E7 and HLA-A2, pulsed with the E7$_{11\text{-}19}$ peptide, or a combination thereof).

The phrase "antigenic specificity," as used herein, means that the TCR (including functional portions and functional variants thereof) can specifically bind to and immunologically recognize HPV 16 E7 with high avidity. For example, a TCR (including functional portions and functional variants thereof) may be considered to have "antigenic specificity" for HPV 16 E7 if T cells expressing the TCR (or functional portion or functional variant thereof) secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, or 20,000 pg/mL or more) of IFN-γ upon co-culture with antigen-negative HLA-A2$^+$ target cells pulsed with a low concentration of HPV 16 E7 peptide (e.g., about 0.05 ng/mL to about 5 ng/mL, 0.05 ng/mL, 0.1 ng/mL, 0.5 ng/mL, 1 ng/mL, or 5 ng/mL). Alternatively or additionally, a TCR (including functional portions and functional variants thereof) may be considered to have "antigenic specificity" for HPV 16 E7 if T cells expressing the TCR (or functional portion or functional variant thereof) secrete at least twice as much IFN-γ as the untransduced peripheral blood lymphocyte (PBL) background level of IFN-γ upon co-culture with antigen-negative HLA-A2$^+$ target cells pulsed with a low concentration of HPV 16 E7 peptide. Cells expressing the inventive TCRs (including functional portions and functional variants thereof) may also secrete IFN-γ upon co-culture with antigen-negative HLA-A2$^+$ target cells pulsed with higher concentrations of HPV 16 E7 peptide.

The invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for HPV 16 E7.

In an embodiment of the invention, the TCR comprises two polypeptide chains, each of which comprises a human variable region comprising a complementarity determining region (CDR)1, a CDR2, and a CDR3 of a TCR. In an embodiment of the invention, the TCR comprises a first polypeptide chain comprising a CDR1 comprising the amino acid sequence of SEQ ID NO: 3 (CDR1 of α chain), a CDR2 comprising the amino acid sequence of SEQ ID NO: 4 (CDR2 of α chain), and a CDR3 comprising the amino acid sequence of SEQ ID NO: 5 (CDR3 of α chain), and a second polypeptide chain comprising a CDR1 comprising the amino acid sequence of SEQ ID NO: 6 (CDR1 of β chain), a CDR2 comprising the amino acid sequence of SEQ ID NO: 7 (CDR2 of β chain), and a CDR3 comprising the amino acid sequence of SEQ ID NO: 8 (CDR3 of β chain). In this regard, the inventive TCR can comprise any one or more of the amino acid sequences selected from the group consisting of SEQ ID NOs: 3-8. Preferably, the TCR comprises SEQ ID NOs: 3-5 or SEQ ID NOs: 6-8. In an especially preferred embodiment, the TCR comprises the amino acid sequences of SEQ ID NOs: 3-8.

In an embodiment of the invention, the TCR can comprise an amino acid sequence of a variable region of a TCR comprising the CDRs set forth above. In this regard, the TCR can comprise the amino acid sequence of SEQ ID NO: 9 (the variable region of a human α chain); SEQ ID NO: 10, wherein X at position 2 of SEQ ID NO: 10 is Ala or Gly (the variable region of aβ chain); both SEQ ID NOs: 9 and 10, wherein X at position 2 of SEQ ID NO: 10 is Ala or Gly; SEQ ID NO: 11 (the variable region of a human β chain); or both SEQ ID NOs: 9 and 11. SEQ ID NO: 10 corresponds to SEQ ID NO: 11 when X at position 2 of SEQ ID NO: 10 is Gly. Preferably, the inventive TCR comprises the amino acid sequences of both SEQ ID NOs: 9 and 10, wherein X at position 2 of SEQ ID NO: 10 is Ala.

The inventive TCRs may further comprise a constant region derived from any suitable species such as, e.g., human or mouse. In an embodiment of the invention, the TCRs further comprise a human constant region. In this regard, the TCR can comprise the amino acid sequence of SEQ ID NO: 14 (the constant region of a human α chain), SEQ ID NO: 15 (the constant region of a human β chain), or both SEQ ID NOs: 14 and 15.

In an embodiment of the invention, the inventive TCR may comprise a combination of a variable region and a constant region. In this regard, the TCR can comprise an alpha chain comprising the amino acid sequences of both of SEQ ID NO: 9 (the variable region of a human α chain) and SEQ ID NO: 14 (the constant region of a human α chain); a beta chain comprising the amino acid sequences of both of SEQ ID NO: 11 (the variable region of a human β chain) and SEQ ID NO: 15 (the constant region of a human β chain); a beta chain comprising the amino acid sequences of both of SEQ ID NO: 10, wherein X at position 2 of SEQ ID NO: 2 is Ala or Gly (the variable region of a β chain) and SEQ ID NO: 15 (the constant region of a human β chain); the amino acid sequences of all of SEQ ID NOs: 9, 11, 14, and 15; or the amino acid sequences of all of SEQ ID NOs: 9, 10, 14, and 15.

In an embodiment of the invention, the inventive TCR can comprise an α chain of a TCR and a β chain of a TCR. Each of the α chain and β chain of the inventive TCR can independently comprise any amino acid sequence. In this regard, the α chain of the inventive TCR can comprise the amino acid sequence of SEQ ID NO: 12. An α chain of this type can be paired with any β chain of a TCR. In this regard, the β chain of the inventive TCR can comprise the amino acid sequence of SEQ ID NO: 13. The inventive TCR, therefore, can comprise the amino acid sequence of SEQ ID NO: 12, SEQ ID NO: 13, or both SEQ ID NOs: 12 and 13. Preferably, the inventive TCR is a human TCR comprising the amino acid sequences of both SEQ ID NOs: 12 and 13.

Another embodiment of the invention provides a chimeric TCR comprising a human variable region and a murine constant region, or a functional variant of the TCR, wherein the TCR and the functional variant have antigenic specificity for human papillomavirus (HPV) 16 E7. The chimeric TCR, or functional variant thereof, may comprise any of the CDR regions as described herein with respect to other aspects of the invention. In another embodiment of the invention, the chimeric TCR, or functional variant thereof, may comprise any of the variable regions described herein with respect to other aspects of the invention.

As used herein, the term "murine" or "human," when referring to a TCR or any component of a TCR described herein (e.g., complementarity determining region (CDR), variable region, constant region, alpha chain, and/or beta chain), means a TCR (or component thereof) which is derived from a mouse or a human, respectively, i.e., a TCR (or component thereof) that originated from or was, at one time, expressed by a mouse T cell or a human T cell, respectively.

In an embodiment of the invention, the inventive chimeric TCRs comprise a murine constant region. In this regard, the TCR can comprise the amino acid sequence of SEQ ID NO: 17 (the constant region of a murine α chain), SEQ ID NO: 19 (the constant region of a murine β chain), or both SEQ ID NOs: 17 and 19. In a preferred embodiment, the inventive TCRs are chimeric TCRs comprising both a human variable region and a murine constant region.

In an embodiment of the invention, the inventive chimeric TCR may comprise a combination of a variable region and a constant region. In this regard, the TCR can comprise an alpha chain comprising the amino acid sequences of both of SEQ ID NO: 9 (the variable region of a human α chain) and SEQ ID NO: 17 (the constant region of a murine α chain); a beta chain comprising the amino acid sequences of both of SEQ ID NO: 11 (the variable region of a human β chain) and SEQ ID NO: 19 (the constant region of a murine β chain); a beta chain comprising the amino acid sequences of both of SEQ ID NO: 10, wherein X at position 2 of SEQ ID NO: 10 is Ala or Gly (the variable region of a β chain) and SEQ ID NO: 19 (the constant region of a murine β chain); the amino acid sequences of all of SEQ ID NOs: 9, 11, 17, and 19; or the amino acid sequences of all of SEQ ID NOs: 9, 10, 17, and 19. In an embodiment, the inventive chimeric TCR comprises a full-length beta chain comprising SEQ ID NO: 20. In this regard, the TCR can comprise all of SEQ ID NOs: 9, 17, and 20.

Included in the scope of the invention are functional variants of the inventive TCRs described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to HPV 16 E7 for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

In an embodiment of the invention, the functional variant comprises the amino acid sequence of any of the TCRs described herein with one, two, three, or four amino acid substitution(s) in the constant region of the alpha or beta chain. Preferably, the functional variant comprises the amino acid sequence of any of the murine constant regions described herein with one, two, three, or four amino acid substitution(s) in the murine constant region. In some embodiments, the TCRs (or functional portions thereof) comprising the substituted amino acid sequence(s) advantageously provide one or more of increased recognition of HPV 16 E7$^+$ targets, increased expression by a host cell, and increased anti-tumor activity as compared to the parent TCR comprising an unsubstituted amino acid sequence. In general, the substituted amino acid sequences of the murine constant regions of the TCR α and β chains, SEQ ID NOs: 16 and 18, respectively, correspond with all or portions of the unsubstituted murine constant region amino acid sequences SEQ ID NOs: 17 and 19, respectively, with SEQ ID NO: 16 having one, two, three, or four amino acid substitution(s) when compared to SEQ ID NO: 17 and SEQ ID NO: 18 having one amino acid substitution when compared to SEQ ID NO: 19. In this regard, an embodiment of the invention provides a functional variant of a TCR comprising the amino acid sequences of (a) SEQ ID NO: 16 (constant region of alpha chain), wherein (i) X at position 48 is Thr or Cys; (ii) X at position 112 is Ser, Gly, Ala, Val, Leu, Ile, Pro, Phe, Met, or Trp; (iii) X at position 114 is Met, Gly, Ala, Val, Leu, Ile, Pro, Phe, Met, or Trp; and (iv) X at position 115 is Gly, Ala, Val, Leu, Ile, Pro, Phe, Met, or Trp; and (b) SEQ ID NO: 18 (constant region of beta chain), wherein X at position 56 is Ser or Cys. In an embodiment of the invention, the functional variant of the TCR comprising SEQ ID NO: 16 does not comprise SEQ ID NO: 17 (unsubstituted murine constant region of alpha chain). In an embodiment of the invention, the functional variant of the TCR comprising SEQ ID NO: 18 does not comprise SEQ ID NO: 19 (unsubstituted murine constant region of beta chain).

In an embodiment of the invention, the substituted amino acid sequence includes cysteine substitutions in the constant region of one or both of the α and β chains to provide a cysteine-substituted TCR. Opposing cysteines in the α and the β chains provide a disulfide bond that links the constant regions of the α and the β chains of the substituted TCR to one another and which is not present in a TCR comprising the unsubstituted human constant region or the unsubstituted murine constant region. In this regard, the functional variant of the TCR is a cysteine-substituted, chimeric TCR in which one or both of the native Thr48 of SEQ ID NO: 17 and the native Ser56 of SEQ ID NO: 19 may be substituted with Cys. Preferably, both of the native Thr48 of SEQ ID NO: 17 and the native Ser56 of SEQ ID NO: 19 are substituted with Cys. In an embodiment, the cysteine-substituted, chimeric TCR comprises an alpha chain constant region comprising the amino acid sequence of SEQ ID NO: 16, wherein X at position 48 is Cys, X at position 112 is the native Ser, X at position 114 is the native Met, and X at position 115 is the native Gly, and a beta chain constant region comprising the amino acid sequence of SEQ ID NO: 18, wherein X at position 56 is Cys. Preferably, the cysteine-substituted, chimeric TCR comprises an alpha chain constant region comprising the amino acid sequence of SEQ ID NO: 24 and a beta chain constant region comprising the amino acid sequence of SEQ ID NO: 23. The cysteine-substituted, chimeric TCRs of the invention may include the substituted constant region in addition to any of the CDRs and/or variable regions described herein. In this regard, the cysteine-substituted, chimeric TCR can comprise the amino acid sequences of (i) SEQ ID NOs: 3-5 and 24; (ii) SEQ ID NO: 9 and 24; (iii) SEQ ID NOs: 6-8 and 23; (iv) SEQ ID NOs: 10 and 23, wherein X at position 2 of SEQ ID NO: 10 is Ala or Gly; (v) SEQ ID NO: 11 and 23; (vi) SEQ ID NOs: 9 and 16; (vii) SEQ ID NOs: 10 and 18; (viii) SEQ ID NOs: 11 and 18; (ix) SEQ ID NOs: 3-5 and 16; or (x) SEQ ID NOs: 6-8 and 18. Preferably, the cysteine-substituted, chimeric TCR comprises the amino acid sequences of (i) SEQ ID NOs: 3-8 and 23-24; (ii) SEQ ID NOs: 9-10 and 23-24; (iii) SEQ ID NOs: 9, 11, and 23-24; (iv) SEQ ID NOs: 3-8, 16, and 18; (v) SEQ ID NOs: 9-10, 16, and 18; or (vi) SEQ ID NOs: 9, 11, 16, and 18. In an embodiment, the Cys-substituted, chimeric TCR comprises a full-length beta chain comprising SEQ ID NO: 27. In this regard, the Cys-substituted, chimeric TCR can comprise SEQ ID NOs: 9 and 24; SEQ ID NO: 27; or all of SEQ ID NOs: 9, 24, and 27.

In an embodiment of the invention, the substituted amino acid sequence includes substitutions of one, two, or three amino acids in the transmembrane (TM) domain of the constant region of one or both of the α and β chains with a hydrophobic amino acid to provide a hydrophobic amino acid-substituted TCR (also referred to herein as an "LVL-modified TCR"). The hydrophobic amino acid substitution(s) in the TM domain of the TCR may increase the hydrophobicity of the TM domain of the TCR as compared to a TCR that lacks the hydrophobic amino acid substitution(s) in the TM domain. In this regard, the functional variant of the TCR is an LVL-modified chimeric TCR in which one, two, or three of the native Ser112, Met114, and Gly115 of SEQ ID NO: 17 may, independently, be substituted with Gly, Ala, Val, Leu, Ile, Pro, Phe, Met, or Trp; preferably with Leu, Ile, or Val. Preferably, all three of the native Ser112, Met114, and Gly115 of SEQ ID NO: 17 may, independently, be substituted with Gly, Ala, Val, Leu, Ile, Pro, Phe, Met, or Trp; preferably with Leu, Ile, or Val. In an embodiment, the LVL-modified chimeric TCR comprises an alpha chain constant region comprising the amino acid sequence of SEQ ID NO: 16, wherein X at position 48 is the native Thr, X at position 112 is Ser, Gly, Ala, Val, Leu, Ile, Pro, Phe, Met, or Trp, X at position 114 is Met, Gly, Ala, Val, Leu, Ile, Pro, Phe, Met, or Trp, and X at position 115 is Gly, Ala, Val, Leu, Ile, Pro, Phe, Met, or Trp, and a beta chain constant region comprising the amino acid sequence of SEQ ID NO: 19, wherein the LVL-modified chimeric TCR comprising SEQ ID NO: 16 does not comprise SEQ ID NO: 17 (unsubstituted murine constant region of alpha chain). Preferably, the LVL-modified, chimeric TCR comprises an alpha chain constant region comprising the amino acid sequence of SEQ ID NO: 21 and a beta chain constant region comprising the amino acid sequence of SEQ ID NO: 19. The LVL-modified, chimeric TCRs of the invention may include the substituted constant region in addition to any of the CDRs and/or variable regions described herein. In this regard, the LVL-modified, chimeric TCR can comprise (i) SEQ ID NOs: 3-5 and 21; (ii) SEQ ID NOs: 9 and 21; (iii) SEQ ID NOs: 6-8 and 19; (iv) SEQ ID NOs: 10 and 19, wherein X at position 2 of SEQ ID NOs: 10 is Ala or Gly; (v) SEQ ID NOs: 11 and 19; (vi) SEQ ID NOs: 9 and 16; (vii) SEQ ID NOs: 3-5 and 16; (x) SEQ ID NOs: 6-8 and 18; (viii) SEQ ID NO: 10 and 18; or (ix) SEQ ID NO: 11 and 18. Preferably, the cysteine-substituted, chimeric TCR comprises the amino acid sequences of (i) SEQ ID NOs: 3-8 and 19 and 21; (ii) SEQ ID NOs: 9-10 and 19 and 21; (iii) SEQ ID NOs: 9, 11, and 19 and 21; (iv) SEQ ID NOs: 3-8, 16, and 18; (v) SEQ ID NOs: 9-10, 16, and 18; or (vi) SEQ ID NOs: 9, 11, 16, and 18. In an embodiment, the LVL-modified, chimeric TCR comprises a full-length alpha chain comprising the amino acid sequence of SEQ ID NO: 22 and a full-length beta chain comprising the amino acid sequence of SEQ ID NO: 20. In this regard, the LVL-modified, chimeric TCR can comprise SEQ ID NO: 20, SEQ ID NO: 22, SEQ ID NO: 29, or both SEQ ID NOs: 20 and 22.

In an embodiment of the invention, the substituted amino acid sequence includes the cysteine substitutions in the constant region of one or both of the α and β chains in combination with the substitution(s) of one, two, or three amino acids in the transmembrane (TM) domain of the constant region of one or both of the α and β chains with a hydrophobic amino acid (also referred to herein as "cysteine-substituted, LVL-modified TCR"). In this regard, the functional variant of the TCR is a cysteine-substituted, LVL-modified, chimeric TCR in which the native Thr48 of SEQ ID NO: 17 is substituted with Cys; one, two, or three of the native Ser112, Met114, and Gly115 of SEQ ID NO: 17 are, independently, substituted with Gly, Ala, Val, Leu, Ile, Pro, Phe, Met, or Trp; preferably with Leu, Ile, or Val; and the native Ser56 of SEQ ID NO: 19 is substituted with Cys. Preferably, all three of the native Ser112, Met114, and Gly115 of SEQ ID NO: 17 may, independently, be substituted with Gly, Ala, Val, Leu, Ile, Pro, Phe, Met, or Trp; preferably with Leu, Ile, or Val. In an embodiment, the cysteine-substituted, LVL-modified, chimeric TCR comprises an alpha chain constant region comprising the amino acid sequence of SEQ ID NO: 16, wherein X at position 48 is Cys, X at position 112 is Ser, Gly, Ala, Val, Leu, Ile, Pro, Phe, Met, or Trp, X at position 114 is Met, Gly, Ala, Val, Leu, Ile, Pro, Phe, Met, or Trp, and X at position 115 is Gly, Ala, Val, Leu, Ile, Pro, Phe, Met, or Trp, and a beta chain constant region comprising the amino acid sequence of SEQ ID NO: 18, wherein X at position 56 is Cys, wherein the cysteine-substituted, LVL-modified chimeric TCR comprising SEQ ID NO: 16 does not comprise SEQ ID NO: 17 (unsubstituted murine constant region of alpha chain). Preferably, the cysteine-substituted, LVL-modified, chimeric TCR comprises an alpha chain constant region comprising the amino acid sequence of SEQ ID NO: 25 and a beta chain constant region comprising the amino acid sequence of SEQ ID NO: 23. The cysteine-substituted, LVL-modified, chimeric TCRs of the invention may include the substituted constant region in addition to any of the CDRs and/or variable regions described herein. In this regard, the cysteine-substituted, LVL-modified, chimeric TCR can comprise (i) SEQ ID NOs: 3-5 and 25; (ii) SEQ ID NO: 9 and 25; (iii) SEQ ID NOs: 6-8 and 23; (iv) SEQ ID NO: 10 and 23, wherein X at position 2 of SEQ ID NO: 10 is Ala or Gly; (v) SEQ ID NO: 11 and 23; (vi) SEQ ID NO: 3-5 and 16; (vii) SEQ ID NOs: 9 and 16; (viii) SEQ ID NOs: 6-8 and 18; (ix) SEQ ID NOs: 10 and 18; or (x) SEQ ID NOs: 11 and 18. Preferably, the cysteine-substituted, LVL-modified, chimeric TCR comprises the amino acid sequences of (i) SEQ ID NOs: 3-8 and 23 and 25; (ii) SEQ ID NOs: 9-10 and 23 and 25; (iii) SEQ ID NOs: 9, 11, and 23 and 25; (iv) SEQ ID NOs: 3-8, 16, and 18; (v) SEQ ID NOs: 9, 10, 16, and 18; or SEQ ID NOs: 9, 11, 16, and 18. In an especially preferred embodiment, the cysteine-substituted, LVL-modified, chimeric TCR comprises a full-length alpha chain comprising the amino acid sequence of SEQ ID NO: 26 and a full-length beta chain comprising the amino acid sequence of SEQ ID NO: 27. In this regard, the Cys-substituted, LVL-modified, chimeric TCR can comprise SEQ ID NO: 26, SEQ ID NO: 27, SEQ ID NO: 30, or both SEQ ID NOs: 26 and 27.

The TCR (or functional variant thereof), polypeptide, or protein can consist essentially of the specified amino acid sequence or sequences described herein, such that other components of the TCR (or functional variant thereof), polypeptide, or protein, e.g., other amino acids, do not materially change the biological activity of the TCR (or functional variant thereof), polypeptide, or protein. In this regard, the inventive TCR (or functional variant thereof), polypeptide, or protein can, for example, consist essentially of the amino acid sequence of any one of SEQ ID NOs: 12, 13, 20, 22, 26, 27, 29, and 30. Also, for instance, the inventive TCRs (including functional variants thereof), polypeptides, or proteins can consist essentially of the amino acid sequence(s) of SEQ ID NO: 9, 10, 11, 14-19, 21, 23-25, both SEQ ID NOs: 9 and 10, both SEQ ID NOs: 9 and 11, both SEQ ID NOs: 14 and 15, both SEQ ID NOs: 16 and 18, both SEQ ID NOs: 17 and 19, both SEQ ID NOs: 23 and 24, both SEQ ID NOs: 19 and 21, or both SEQ ID NOs: 23 and 25. Furthermore, the inventive TCRs (including functional variants thereof), polypeptides, or proteins can consist essentially of the amino acid sequence of SEQ ID NO: 3 (CDR1 of α chain), SEQ ID NO: 4 (CDR2 of α chain), SEQ ID NO: 5 (CDR3 of α chain), SEQ ID NO: 6 (CDR1 of β chain), SEQ ID NO: 7 (CDR2 of β chain), SEQ ID NO: 8 (CDR3 of β chain), or any combination thereof, e.g., SEQ ID NOs: 3-5; 6-8; or 3-8.

Also provided by the invention is a polypeptide comprising a functional portion of any of the TCRs (or functional variants thereof) described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR (or functional variant thereof) of which it is a part, provided that the functional portion specifically binds to HPV 16 E7. The term "functional portion" when used in reference to a TCR (or functional variant thereof) refers to any part or fragment of the TCR (or functional variant thereof) of the invention, which part or fragment retains the biological activity of the TCR (or functional variant thereof) of which it is a part (the parent TCR or parent functional variant thereof). Functional portions encompass, for example, those parts of a TCR (or functional variant thereof) that retain the ability to specifically bind to HPV 16 E7 (e.g., in an HLA-A2-dependent manner), or detect, treat, or prevent cancer, to a similar extent, the same extent, or to a higher extent, as the parent TCR (or functional variant thereof). In reference to the parent TCR (or functional variant thereof), the functional portion can comprise, for instance, about 10%, 25%, 30%, 50%, 68%, 80%, 90%, 95%, or more, of the parent TCR (or functional variant thereof).

The functional portion can comprise additional amino acids at the amino or carboxy terminus of the portion, or at both termini, which additional amino acids are not found in the amino acid sequence of the parent TCR or functional variant thereof. Desirably, the additional amino acids do not interfere with the biological function of the functional portion, e.g., specifically binding to HPV 16 E7; and/or having the ability to detect cancer, treat or prevent cancer, etc. More desirably, the additional amino acids enhance the biological activity, as compared to the biological activity of the parent TCR or functional variant thereof.

The polypeptide can comprise a functional portion of either or both of the α and β chains of the TCRs or functional variant thereof of the invention, such as a functional portion comprising one of more of CDR1, CDR2, and CDR3 of the variable region(s) of the α chain and/or β chain of a TCR or functional variant thereof of the invention. In an embodiment of the invention, the polypeptide can comprise a functional portion comprising the amino acid sequence of SEQ ID NO: 3 (CDR1 of α chain), 4 (CDR2 of α chain), 5 (CDR3 of α chain), 6 (CDR1 of β chain), 7 (CDR2 of β chain), 8 (CDR3 of β chain), or a combination thereof.

Preferably, the inventive polypeptide comprises a functional portion comprising SEQ ID NOs: 3-5; 6-8; or all of SEQ ID NOs: 3-8. More preferably, the polypeptide comprises a functional portion comprising the amino acid sequences of all of SEQ ID NOs: 3-8.

In an embodiment of the invention, the inventive polypeptide can comprise, for instance, the variable region of the inventive TCR or functional variant thereof comprising a combination of the CDR regions set forth above. In this regard, the polypeptide can comprise the amino acid sequence of SEQ ID NO: 9 (the variable region of an α chain), SEQ ID NO: 10, wherein X at position 2 of SEQ ID NO: 10 is Ala or Gly (the variable region of a β chain), SEQ ID NO: 11 (the variable region of a β chain), both SEQ ID NOs: 9 and 10, or both SEQ ID NOs: 9 and 11. Preferably, the polypeptide comprises the amino acid sequences of both SEQ ID NOs: 9 and 10, wherein X at position 2 of SEQ ID NO: 10 is Ala.

The inventive polypeptide may further comprise a constant region derived from any suitable species such as, e.g., human or mouse, described herein or any of the substituted constant regions described herein. In this regard, the polypeptide can comprise the amino acid sequence of SEQ ID NO: 14 (the constant region of a human α chain), SEQ ID NO: 15 (the constant region of a human β chain), SEQ ID NO: 16 (constant region of α chain, substituted as described herein with respect to other aspects of the invention), SEQ ID NO: 17 (the constant region of a murine α chain), SEQ ID NO: 18 (constant region of β chain, substituted as described herein with respect to other aspects of the invention), SEQ ID NO: 19 (the constant region of a murine β chain), SEQ ID NO: 21 (constant region of an LVL-modified α chain), SEQ ID NO: 23 (constant region of a Cys-substituted β chain), SEQ ID NO: 24 (constant region of a Cys-substituted α chain), SEQ ID NO: 25 (constant region of a Cys-substituted, LVL-modified α chain), both SEQ ID NOs: 14 and 15, both SEQ ID NOs: 16 and 18, both SEQ ID NOs: 17 and 19, both SEQ ID NOs: 19 and 21, both SEQ ID NOs: 23 and 24, or both SEQ ID NOs: 23 and 25. Preferably, the polypeptide comprises both SEQ ID NOs: 14 and 15, both SEQ ID NOs: 16 and 18, both SEQ ID NOs: 17 and 19, both SEQ ID NOs: 19 and 21, both SEQ ID NOs: 23 and 24, or both SEQ ID NOs: 23 and 25. In an embodiment, the polypeptide comprising the amino acid sequence of one or both of SEQ ID NOs: 9 and 11 is isolated or purified.

In an embodiment of the invention, the inventive polypeptide may comprise a combination of a variable region and a constant region. In this regard, the polypeptide can comprise both SEQ ID NOs: 9 and 14, both SEQ ID NOs: 9 and 16, both SEQ ID NOs: 9 and 17, both SEQ ID NOs: 9 and 21, both SEQ ID NOs: 9 and 24, both SEQ ID NOs: 9 and 25, both SEQ ID NOs: 10 and 15, both SEQ ID NOs: 10 and 18, both SEQ ID NOs: 10 and 19, both SEQ ID NOs: 10 and 23, both SEQ ID NOs: 11 and 15, both SEQ ID NOs: 11 and 18, both SEQ ID NOs: 11 and 19, both SEQ ID NOs: 11 and 23, all of SEQ ID NOs: 3-5 and 14, all of SEQ ID NOs: 3-5 and 16, all of SEQ ID NOs: 3-5 and 17, all of SEQ ID NOs: 3-5 and 21, all of SEQ ID NOs: 3-5 and 24, all of SEQ ID NOs: 3-5 and 25, all of SEQ ID NOs: 6-8 and 15, all of SEQ ID NOs: 6-8 and 18, all of SEQ ID NOs: 6-8 and 19, all of SEQ ID NOs: 6-8 and 23, all of SEQ ID NOs: 3-8 and 14-15, all of SEQ ID NOs: 3-8 and 16 and 18, all of SEQ ID NOs: 3-8 and 17 and 19, all of SEQ ID NOs: 3-8 and 19 and 21, all of SEQ ID NOs: 3-8 and 23 and 24, all of SEQ ID NOs: 3-8 and 23 and 25, all of SEQ ID NOs: 9-10 and 14-15, all of SEQ ID NOs: 9-10 and 16 and 18, all of SEQ ID NOs: 9-10 and 17 and 19, all of SEQ ID NOs: 9-10 and 19 and 21, all of SEQ ID NOs: 9-10 and 23 and 24, all of SEQ ID NOs: 9-10 and 23 and 25, all of SEQ ID NOs: 9, 11, and 14-15, all of SEQ ID NOs: 9, 11, and 16 and 18, all of SEQ ID NOs: 9, 11, and 17 and 19, all of SEQ ID NOs: 9, 11, and 19 and 21, all of SEQ ID NOs: 9, 11, and 23 and 24, or all of SEQ ID NOs: 9, 11, and 23 and 25. SEQ ID NOs: 16 and 18 may be substituted as described herein with respect to other aspects of the invention. In an embodiment, the polypeptide comprising the amino acid sequence of one or both of (i) SEQ ID NOs: 9 and 14 and (ii) SEQ ID NOs: 11 and 15 is isolated or purified.

In an embodiment of the invention, the inventive polypeptide can comprise the entire length of an α or β chain of one of the TCRs or functional variant thereof described herein. In this regard, the inventive polypeptide can comprise an amino acid sequence of (i) any one of SEQ ID NOs: 12, 13, 20, 22, 26, 27, 29, 30; (ii) SEQ ID NOs: 9, 24, and 27; (iii) SEQ ID NOs: 9, 17, and 20; or (iv) SEQ ID NOs: 9, 10, 16, and 18. SEQ ID NOs: 16 and 18 may be substituted as described herein with respect to other aspects of the invention.

Alternatively, the polypeptide of the invention can comprise α and β chains of the TCRs or functional variants thereof described herein. For example, the inventive polypeptide can comprise the amino acid sequences of both SEQ ID NOs: 12 and 13; both SEQ ID NOs: 20 and 22; both SEQ ID NOs: 26 and 27; all of SEQ ID NOs: 9, 24, and 27; all of SEQ ID NOs: 9, 17, and 20; or all of SEQ ID NOs: 9, 10, 16, and 18. Preferably, the polypeptide comprises the amino acid sequences of both SEQ ID NOs: 12 and 13; both SEQ ID NOs: 20 and 22; both SEQ ID NOs: 26 and 27; all of SEQ ID NOs: 9, 24, and 27; all of SEQ ID NOs: 9, 17, and 20; or all of SEQ ID NOs: 9, 10, 16, and 18. SEQ ID NOs: 16 and 18 may be substituted as described herein with respect to other aspects of the invention. In an embodiment, the polypeptide comprising the amino acid sequence of one or both of SEQ ID NOs: 12 and 13 is isolated or purified.

The invention further provides a protein comprising at least one of the polypeptides described herein. By "protein" is meant a molecule comprising one or more polypeptide chains. In an embodiment, the protein comprising (a) one or both of the amino acid sequences of SEQ ID NO: 9 and SEQ ID NO: 10, wherein X at position 2 of SEQ ID NO: 10 is Gly, or (b) one or both of SEQ ID NO: 12 and 13 is isolated or purified.

In an embodiment, the protein of the invention can comprise a first polypeptide chain comprising the amino acid sequences of SEQ ID NOs: 3-5 and a second polypeptide chain comprising the amino acid sequence of SEQ ID NOs: 6-8. Alternatively or additionally, the protein of the invention can comprise a first polypeptide chain comprising the amino acid sequence of SEQ ID NO: 9 and a second polypeptide chain comprising the amino acid sequence of SEQ ID NO: 10, wherein (i) X at position 2 of SEQ ID NO: 10 is Ala or Gly, and (ii) the protein comprising SEQ ID NOs: 9 and 10, wherein X at position 2 of SEQ ID NO: 10 is Gly, is isolated or purified. The protein can, for example, comprise a first polypeptide chain comprising the amino acid sequence of (i) SEQ ID NO: 12, (ii) SEQ ID NO: 22, (iii) SEQ ID NO: 26, (iv) SEQ ID NO: 9 and 16, (v) SEQ ID NO: 9 and 17, or (vi) SEQ ID NO: 9 and 24 and a second polypeptide chain comprising the amino acid sequence of (i) SEQ ID NO: 10 and 18, or (ii) any one of SEQ ID NOs: 13, 20, and 27, wherein the protein comprising SEQ ID NO: 12 and 13 is isolated or purified, and SEQ ID NOs: 16 and 18 are substituted as described herein with respect to other aspects of the invention. In this instance, the protein of the invention can be a TCR. Alternatively, if, for example, the protein comprises a single polypeptide chain comprising both SEQ ID NOs: 12 and 13, both SEQ ID NO: 20 and 22, SEQ ID NO: 26 and 27, all of SEQ ID NOs: 9, 10, 16, and 18, all of SEQ ID NOs: 9, 17, and 20, all of SEQ ID NOs: 9, 24, and 27, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., *Mol. Biotechnol.* 31: 193-202 (2005).

In some embodiments of the invention, the TCRs (and functional portions and functional variants thereof), polypeptides, and proteins of the invention may be expressed as a single protein comprising a linker peptide linking the α chain and the β chain. In this regard, the TCRs (and functional variants and functional portions thereof), polypeptides, and proteins of the invention comprising both SEQ ID NOs: 12 and 13, both SEQ ID NO: 20 and 22, SEQ ID NO: 26 and 27, all of SEQ ID NOs: 9, 10, 16, and 18, all of SEQ ID NOs: 9, 17, and 20, all of SEQ ID NOs: 9, 24, and 27 may further comprise a linker peptide. The linker peptide may advantageously facilitate the expression of a recombinant TCR (including functional portions and functional variants thereof), polypeptide, and/or protein in a host cell. The linker peptide may comprise any suitable amino acid sequence. For example, the linker peptide may comprise SEQ ID NO: 28. In an embodiment of the invention, the protein comprising an alpha chain, beta chain, and a linker may comprise SEQ ID NO: 29 (LVL-modified, chimeric TCR) or SEQ ID NO: 30 (Cys-substituted, LVL-modified, chimeric TCR). Upon expression of the construct including the linker peptide by a host cell, the linker peptide may be cleaved, resulting in separated α and β chains.

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)₂' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

The TCRs, polypeptides, and proteins of the invention (including functional variants thereof) can be of any length, i.e., can comprise any number of amino acids, provided that the TCRs, polypeptides, or proteins (or functional variants thereof) retain their biological activity, e.g., the ability to specifically bind to HPV 16 E7; detect cancer, HPV 16 infection, or HPV-positive premalignancy in a mammal; or treat or prevent cancer, HPV 16 infection, or HPV-positive premalignancy in a mammal, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention (including functional variants thereof) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention (including functional variants thereof) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention (including functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Green and Sambrook, *Molecular Cloning: A Laboratory Manual*, 4th ed., Cold Spring Harbor Press, Cold Spring Harbor, N.Y. 2012; and Ausubel et al., *Current Protocols in Molecular Biology*, Greene Publishing Associates and John Wiley & Sons, N Y, 1994. Further, some of the TCRs, polypeptides, and proteins of the invention (including functional variants thereof) can be isolated and/or purified from a source, such as a plant, a bacterium, an insect, a mammal, e.g., a rat, a human, etc. Methods of isolation and purification are well-known in the art. Alternatively, the TCRs, polypeptides, and/or proteins described herein (including functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs (including functional variants thereof), polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

An embodiment of the invention provides a nucleic acid sequence comprising a nucleotide sequence encoding any of the TCRs (including functional portions and functional variants thereof, polypeptides, or proteins described herein. By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, proteins, or functional variants thereof described herein. In an embodiment of the invention, the nucleotide sequence may comprise, consist, or consist essentially of any one of SEQ ID NO: 31 (alpha chain of human, wild-type TCR), SEQ ID NO: 32 (beta chain of human, wild-type TCR), SEQ ID NO: 33 (alpha chain of LVL-modified, chimeric TCR), SEQ ID NO: 34 (beta chain of chimeric TCR), SEQ ID NO: 35 (alpha chain of Cys-substituted, LVL-modified, chimeric TCR), SEQ ID NO: 36 (beta chain of Cys-substituted, chimeric TCR), both SEQ ID NOs: 31 and 32, both SEQ ID NOs: 33 and 34, or both SEQ ID NOs: 35 and 36.

In an embodiment of the invention, the nucleic acid comprises a non-natural nucleotide sequence. A nucleotide sequence may be considered to be "non-natural" if the nucleotide sequence is not found in nature. In some embodiments, the nucleotide sequence may be codon-optimized. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency. In an embodiment of the invention, the codon-optimized nucleotide sequence may comprise, consist, or consist essentially of any one of SEQ ID NOs: 33-36, both of SEQ ID NOs: 33 and 34, or both of SEQ ID NOs: 35 and 36.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs (including functional portions and functional variants thereof). It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

The nucleic acids of the invention can be incorporated into a recombinant expression vector. In this regard, the invention provides recombinant expression vectors comprising any of the nucleic acids of the invention. In an embodiment of the invention, the recombinant expression vector comprises a nucleotide sequence encoding the α chain, the β chain, and linker peptide. For example, in an embodiment, the recombinant expression vector comprises a codon-optimized nucleotide sequence comprising SEQ ID NO: 39 (encoding chimeric α and β chains SEQ ID NOs: 20 and 22 with a linker positioned between them, wherein the nucleotide sequence encoding the beta chain is positioned 5' of the nucleotide sequence encoding the alpha chain) or SEQ ID NO: 40 (encoding chimeric α and β chains SEQ ID NOs: 26 and 27 with a linker positioned between them, wherein the nucleotide sequence encoding the beta chain is positioned 5' of the nucleotide sequence encoding the alpha chain).

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector. In an especially preferred embodiment, the recombinant expression vector is an MSGV1 vector.

In a preferred embodiment, the recombinant expression vector comprises a nucleotide sequence encoding an alpha chain and a beta chain of any of the TCRs (including functional portions and functional variants thereof) described herein, wherein the nucleotide sequence encoding the beta chain is positioned 5' of the nucleotide sequence encoding the alpha chain. In this regard, the nucleotide sequence encoding the alpha chain may be positioned 3' of the nucleotide sequence encoding the beta chain. Without being bound by a particular theory or mechanism, it is believed that a nucleotide sequence encoding a beta chain that is positioned 5' of the nucleotide sequence encoding the alpha chain may provide any one or more of increased recognition of HPV 16 E7+ targets, increased expression by a host cell, and increased anti-tumor activity as compared to a nucleotide sequence encoding a beta chain that is positioned 3' of the nucleotide sequence encoding the alpha chain. In a less preferred embodiment, the nucleotide sequence encoding the beta chain is positioned 3' of the nucleotide sequence encoding the alpha chain. In this regard, the nucleotide sequence encoding the alpha chain may be positioned 5' of the nucleotide sequence encoding the beta chain. In an embodiment, an MSGV1 vector comprising a codon-optimized nucleotide sequence encoding an LVL-modified, chimeric TCR comprising SEQ ID NOs: 20 and 22 of the invention, wherein the nucleotide sequence encoding the beta chain is positioned 5' of the nucleotide sequence encoding the alpha chain, comprises SEQ ID NO: 37. In another embodiment, an MSGV1 vector comprising a codon-optimized nucleotide sequence encoding a Cys-substituted, LVL-modified, chimeric TCR comprising SEQ ID NOs: 26 and 27 of the invention, wherein the nucleotide sequence encoding the beta chain is positioned 5' of the nucleotide sequence encoding the alpha chain, comprises SEQ ID NO: 38.

The recombinant expression vectors of the invention can be prepared using standard recombinant DNA techniques described in, for example, Green and Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2 μ, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein (including functional variants thereof), or to the nucleotide sequence which is complementary to or which hybridizes to the nucleotide sequence encoding the TCR, polypeptide, or protein (including functional variants thereof). The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, $CD4^+$/$CD8^+$ double positive T cells, $CD4^+$ helper T cells, e.g., $Th_1$ and $Th_2$ cells, $CD4^+$ T cells, $CD8^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990).

The invention further provides an antibody, or antigen binding portion thereof, which specifically binds to a functional portion of any of the TCRs (or functional variant thereof) described herein. Preferably, the functional portion specifically binds to the cancer antigen, e.g., the functional portion comprising the amino acid sequence SEQ ID NO: 3 (CDR1 of α chain), 4 (CDR2 of α chain), 5 (CDR3 of α chain), 6 (CDR1 of β chain), 7 (CDR2 of β chain), 8 (CDR3 of β chain), SEQ ID NO: 9 (variable region of α chain), SEQ ID NO: 10 (variable region of β chain), SEQ ID NO: 11 (variable region of β chain), or a combination thereof, e.g., 3-5; 6-8; 3-8; 9; 10; 11; 9-10; or 9 and 11. More preferably, the functional portion comprises the amino acid sequences of SEQ ID NOs: 3-8; SEQ ID NOs: 9 and 10; or SEQ ID NOs: 9 and 11. In a preferred embodiment, the antibody, or antigen binding portion thereof, binds to an epitope which is formed by all 6 CDRs (CDR1-3 of the alpha chain and CDR1-3 of the beta chain). The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive TCR (or functional variant thereof). Desirably, the antibody is specific for the functional portion of the inventive TCR (or functional variants thereof), such that there is minimal cross-reaction with other peptides or proteins.

Methods of testing antibodies for the ability to bind to any functional portion or functional variant of the inventive TCR are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 8th Ed., Garland Publishing, New York, N.Y. (2011)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1.

Phage display furthermore can be used to generate the antibody of the invention. In this regard, phage libraries encoding antigen-binding variable (V) domains of antibodies can be generated using standard molecular biology and recombinant DNA techniques (see, e.g., Green and Sambrook et al. (eds.), *Molecular Cloning, A Laboratory Manual*, 4th Edition, Cold Spring Harbor Laboratory Press, New York (2012)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in, for example, U.S. Pat. No. 5,639,641 and Pedersen et al., *J. Mol. Biol.*, 235, 959-973 (1994).

The invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7, 697-704

(1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive TCRs, polypeptides, proteins, (including functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

The inventive TCRs, polypeptides, proteins (including functional variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, functional portions, functional variants, nucleic acids, expression vectors, host cells (including populations thereof), and antibodies (including antigen binding portions thereof) described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs (including functional portions and functional variants thereof). Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for oral, parenteral, subcutaneous, intravenous, intramuscular, intraarterial, intrathecal, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR (or functional variant or functional portion thereof), polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the condition being treated. In an embodiment in which the inventive TCR material is a population of cells, the number of cells administered per infusion may vary, e.g., from about $1 \times 10^6$ to about $1 \times 10^{12}$ cells or more. In certain embodiments, fewer than $1 \times 10^6$ cells may be administered.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a targeting moiety. The practice of conjugating compounds, e.g., inventive TCR materials, to targeting moieties is known in the art. See, for instance, Wadwa et al., *J. Drug Targeting* 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T cell receptor (TCR), B-cell receptor (BCR), CD28, Platelet-derived Growth Factor Receptor (PDGF), nicotinic acetylcholine receptor (nAChR), etc.). The term "bridge" as used herein, refers to any agent or molecule that links the inventive TCR materials to the targeting moiety. One of ordinary skill in the art recognizes that sites on the inventive TCR materials, which are not necessary for the function of the inventive TCR materials, are ideal sites for attaching a bridge and/or a targeting moiety, provided that the bridge and/or targeting moiety, once attached to the inventive TCR materials, do(es) not interfere with the function of the inventive TCR materials, i.e., the ability to bind to HPV 16 E7; or to detect, treat, or prevent cancer, HPV 16 infection, or HPV-positive premalignancy.

It is contemplated that the inventive pharmaceutical compositions, TCRs (including functional variants thereof), polypeptides, proteins, nucleic acids, recombinant expression vectors, host cells, or populations of cells can be used in methods of treating or preventing cancer, HPV 16 infection, or HPV-positive premalignancy. Without being bound to a particular theory, the inventive TCRs (and functional variants thereof) are believed to bind specifically to HPV 16 E7, such that the TCR (or related inventive polypeptide or protein and functional variants thereof), when expressed by a cell, is able to mediate an immune response against a target cell expressing HPV 16 E7. In this regard, the invention provides a method of treating or preventing a condition in a mammal, comprising administering to the mammal any of the pharmaceutical compositions, TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a recombinant vector which encodes any of the TCRs (and functional variants thereof), polypeptides, or proteins described herein, in an amount effective to treat or prevent the condition in the mammal, wherein the condition is cancer, HPV 16 infection, or HPV-positive premalignancy.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a mammal. Furthermore, the treatment or prevention provided by the inventive method can include treatment or prevention of one or more conditions or symptoms of the condition, e.g., cancer, being treated or prevented. For example, treatment or prevention can include promoting the regression of a tumor. Also, for purposes herein, "prevention" can encompass delaying the onset of the condition, or a symptom or condition thereof.

Also provided is a method of detecting the presence of a condition in a mammal. The method comprises (i) contacting a sample comprising one or more cells from the mammal with any of the inventive TCRs (and functional variants thereof), polypeptides, proteins, nucleic acids, recombinant expression vectors, host cells, populations of cells, antibodies, or antigen binding portions thereof, or pharmaceutical compositions described herein, thereby forming a complex, and detecting the complex, wherein detection of the complex is indicative of the presence of the condition in the mammal, wherein the condition is cancer, HPV 16 infection, or HPV-positive premalignancy.

With respect to the inventive method of detecting a condition in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs (and functional variants thereof), polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is cancer of the uterine cervix, oropharynx, anus, anal canal, anorectum, vagina, vulva, or penis. A particularly preferred cancer is HPV 16-positive cancer. While the cancers most commonly associated with HPV 16 infection include cancer is cancer of the uterine cervix, oropharynx, anus, anal canal, anorectum, vagina, vulva, and penis, the inventive methods may be used to treat any HPV 16-positive cancer, including those that occur at other anatomical areas.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

Example 1

This example demonstrates the isolation of a human anti-HPV 16 E7 TCR from neoplasia.

Samples of lymphocytes from HPV 16-positive cervical intraepithelial neoplasia (CIN) II/III were obtained from fourteen patients. The patients had previously received various vaccines targeting HPV 16 E7. Numbers of cervix infiltrating lymphocytes (CIL) were expanded using the Rapid Expansion Protocol (REP) as previously described (Dudley et al. *J. Immunother.* 26:332-42 (2003) and Riddell et al. *J. Immunol. Methods* 128:189-201 (1990)). Briefly, TIL were cultured with irradiated (40 Gy) allogeneic peripheral blood mononuclear "feeder" cells in complete medium (CM) with 30 ng/mL anti-CD3 antibody and 6000 IU/mL IL-2. The expanded numbers of CIL were screened for HPV 16 E7 reactivity by measuring interferon (IFN)-γ secretion following co-culture with autologous dendritic cells (DCs) pulsed with gp100 peptide, a pool of 15-mer E6 peptides that overlap by 11 amino acid residues and which span the whole length of HPV 16 E6, a pool of 15-mer E7 peptides that overlap by 11 amino acid residues and which span the whole length of HPV 16 E7, or OKT3. The CD8$^+$ CIL of one patient (5048) were identified as having HPV 16 E7 reactivity. The patient 5048 was also found to express HLA-A*02:01.

A tetramer of HLA-A*02:01/E7$_{11-19}$ was used to determine the presence of T cells from patient 5048 targeting the epitope HPV 16 E7$_{11-19}$. Tetramer-binding cells were isolated using magnetic bead separation using anti-PE antibody and limiting dilution cloning was performed. T cells clones were screened for tetramer binding and a high-binding clone was identified.

The variable regions of the alpha and beta chains of the TCR of the clone that bound the HLA-A2/E7$_{11-19}$ tetramer was isolated and sequenced using 5' Rapid Amplification of cDNA Ends (RACE) polymerase chain reaction (PCR). A nucleotide sequence comprising cDNA encoding the variable region of a wild-type human α chain comprising SEQ ID NO: 9 was obtained from TRAV1-2*01/TRAJ7*01. A nucleotide sequence comprising cDNA encoding the variable region of a wild-type human β chain comprising SEQ ID NO: 11 was obtained from TRBV5-6*01/TRBJ2-1/TRBD2.

Example 2

This example demonstrates that peripheral blood T cells transduced to express a chimeric anti-HPV 16 E7 TCR comprising a human variable region and a mouse constant region displayed CD8-independent binding to HLA-A2/E7$_{11-19}$ tetramer and recognized HLA-A2$^+$ HPV-16$^+$ tumor lines.

An MSGV1 recombinant expression vector comprising nucleotide sequences encoding a chimeric anti-HPV 16 E7 TCR comprising a human variable region derived from the wild-type, human TCR of Example 1 and a mouse constant region was prepared as follows. The nucleotide sequences in the recombinant expression vector encoded the variable region of the α chain and the variable region of the β chain of the TCR of Example 1, with the exception that an alanine was substituted for the native glycine in the second position of the variable region of the β chain (the leader sequence) in order to provide a NcoI restriction site and Kozak sequence in the recombinant expression vector. Nucleotide sequences encoding a murine constant region of the α and β chains (SEQ ID NOs: 17 and 19, respectively) were inserted into the vector in place of the respective human constant regions to provide a nucleotide sequence encoding a chimeric TCR. A codon-optimized nucleotide sequence encoding a picornavirus 2A peptide (SEQ ID NO: 28) was positioned between the α and β chains. The nucleotide sequence encoding the chimeric α and β chains and linker were codon-optimized for expression in human tissues.

Peripheral blood cells were transduced with retrovirus from the MSGV1 recombinant expression vector encoding the chimeric TCR or a vector encoding a fully murine, anti-HPV 16 E7 TCR. Untransduced cells were used as a negative control. The transduced cells were labeled with anti-CD8 and anti-TRBC (mouse constant region) antibodies and tested for binding to HLA-A2/E7$_{11-19}$ tetramer by flow cytometry. Untransduced cells (both CD8$^+$ and CD8$^-$) and cells transduced to express a control mouse anti-HPV 16 E7 TCR that was identified in prior experiments (both CD8$^+$ and CD8$^-$) did not bind the tetramer. Both CD8$^+$ and CD8$^-$ cells transduced with the chimeric HPV-16 E7 TCR bound the tetramer. Accordingly, PBL transduced with the chimeric TCR bound HLA-A2/E7$_{11-19}$ tetramer in a CD8-independent manner. It was also observed that about 50% of the transduced T cells expressing the β chain of the chimeric TCR did not bind to tetramer.

In a separate experiment, peripheral blood lymphocytes (PBL) were transduced with the MSGV1 recombinant expression vector encoding the chimeric TCR with approximately 50% transduction efficiency. HLA-A2/E7$_{11-19}$ tetramer binding was measured by fluorescence-activated cell sorting (FACS), and 25% of the cells were found to bind tetramer on day 8 after stimulation. Transduced cells were co-cultured with target 293-A2 cells pulsed with HPV 16 E6$_{29-38}$ peptide (control), 293-A2 cells pulsed with HPV 16 E7$_{11-19}$ peptide, 624 cells transduced with a plasmid encoding HPV 16 E6, 624 cells transduced with a plasmid encoding HPV 16 E7, SCC152 cells, SCC90 cells, CaSki cells, Alb cells, Pancl cells, or SiHa cells 10 days after stimulation. Untransduced cells were used as a control. IFN-γ was measured. The results are shown in FIG. 1. As shown in FIG. 1, PBL transduced with the MSGV1 recombinant expression vector encoding the chimeric TCR specifically recognized HPV 16 E7-positive tumor cell lines and other HLA-A2$^+$HPV16 E7$^+$ targets in an HLA-A2-restricted manner. Results obtained with the cells of a second donor were similar.

Example 3

This example demonstrates a method of making a chimeric anti-HPV 16 E7 TCR comprising a human variable region and a mouse constant region, wherein three native amino acid residues in the transmembrane (TM) region of the constant region of the α chain of the TCR are each substituted with a hydrophobic amino acid residue.

A nucleotide sequence encoding a chimeric TCR comprising a human variable region and a mouse constant region, wherein three native amino acid residues in the transmembrane (TM) region of the constant region of the α chain of the TCR are each substituted with a hydrophobic amino acid residue, was prepared as follows. The nucleotide sequences encoding the α and β chains of the chimeric TCR of Example 2 were cloned into a single nucleotide sequence with the nucleotide sequence encoding the β chain positioned 5' of the nucleotide sequence encoding the alpha chain and a nucleotide sequence encoding a picornavirus 2A peptide (SEQ ID NO: 28) positioned between the α and β chains. With reference to the wild-type α chain mouse constant region SEQ ID NO: 17, three native amino acid residues in the TM region of the α chain (namely, the Ser, Met, and Gly at positions 112, 114, and 115, respectively, were substituted with a Leu, Ile, and Val, respectively. The combined nucleotide sequence was codon-optimized for expression in human tissues to provide a vector insert (SEQ ID NO: 39). The vector insert was cloned into an MSGV1 expression vector resulting in SEQ ID NO: 37. The TCR encoded by the vector comprised an α chain comprising an amino acid sequence comprising SEQ ID NO: 22 and a β chain comprising an amino acid sequence comprising SEQ ID NO: 20 ("LVL-modified TCR" or "LVL TCR").

Example 4

This example demonstrates a method of making chimeric anti-HPV 16 E7 TCRs comprising a human variable region and a mouse constant region, wherein a native amino acid residue in the β and α chains are each substituted with a cysteine residue.

The TCR of Example 2 was modified to include a Cys substitution in the constant region of each of the α and β chains as follows. The nucleotide sequence encoding the constant region of the α chain of the TCR of Example 2 (amino acid SEQ ID NO: 17) was modified to substitute the native Thr at position 48 with Cys. The nucleotide sequence encoding the constant region of the β chain of the TCR of Example 2 (SEQ ID NO: 19) was modified to substitute the native Ser at position 56 with Cys. The nucleotide sequences encoding the α and β chains were cloned into a single nucleotide sequence with the nucleotide sequence encoding the β chain positioned 5' of the nucleotide sequence encoding the α chain and a nucleotide sequence encoding a picornavirus 2A peptide (SEQ ID NO: 28) positioned between the α and β chains. The combined nucleotide sequence was codon-optimized for expression in human tissues to provide a vector insert. The vector insert was cloned into an MSGV1 expression vector. The TCR encoded by the vector comprised an α chain comprising an amino acid sequence comprising SEQ ID NOs: 9 and 24 and a β chain comprising an amino acid sequence comprising SEQ ID NO: 27 ("Cys-modified TCR" or "Cys TCR").

The TCR of Example 3 (LVL-modified TCR) was further modified to include a Cys substitution in the constant region of each of the α and β chains as follows. The nucleotide sequence encoding the constant region of the α chain of the LVL-modified TCR of Example 3 (amino acid SEQ ID NO: 21) was modified to substitute the native Thr at position 48 with Cys. The nucleotide sequence encoding the constant region of the β chain of the LVL-modified TCR of Example 3 (SEQ ID NO: 19) was modified to substitute the native Ser at position 56 with Cys. The nucleotide sequences encoding the α and β chains were cloned into a single nucleotide sequence with the nucleotide sequence encoding the β chain positioned 5' of the nucleotide sequence encoding the α chain and a nucleotide sequence encoding a picornavirus 2A peptide (SEQ ID NO: 28) positioned between the α and β chains. The combined nucleotide sequence was codon-optimized for expression in human tissues to provide a vector insert (SEQ ID NO: 40). The vector insert was cloned into an MSGV1 expression vector resulting in SEQ ID NO: 38. The TCR encoded by the vector comprised an α chain comprising an amino acid sequence comprising SEQ ID NO: 26 and a β chain comprising an amino acid sequence comprising SEQ ID NO: 27 ("LVL-Cys-modified TCR" or "LVL-Cys TCR").

Example 5

This example demonstrates that modification of the recombinant expression vector encoding the chimeric anti-HPV 16 E7 TCR of Example 2 improved HPV 16 E7$_{11-19}$ tetramer binding and improved recognition of HPV 16$^+$ tumor cell lines.

PBL from two donors were transduced with one of the recombinant expression vectors set forth in Table 1.

TABLE 1

| TCR | amino acid SEQ ID NOs of TCR | Position of α and β chain in vector |
| --- | --- | --- |
| chimeric anti-HPV 16 E7 TCR (Example 2) | 9, 10, 17, and 19, wherein X at position 2 of SEQ ID NO: 10 is Ala | alpha chain is positioned 5' of beta chain ("α/β") |
| Cys-modified TCR | 9, 24, 27 | α/β |
| LVL-modified TCR | 20, 22 | α/β |
| LVL-Cys-modified TCR | 26, 27 | α/β |
| chimeric anti-HPV 16 E7 TCR (Example 2) | 9, 10, 17, and 19, wherein X at position 2 of SEQ ID NO: 10 is Ala | beta chain is positioned 5' of alpha chain ("β/α") |
| Cys-modified TCR | 9, 24, 27 | β/α |
| LVL-modified TCR | 20, 22 | β/α |
| LVL-Cys-modified TCR | 26, 27 | β/α |

Transduced PBL from two normal donors were tested for HPV 16 E7$_{11-19}$ tetramer binding by flow cytometry using anti-HPV 16 E7$_{11-19}$ tetramer and anti-mouse(m)TRBC antibodies on day 8 after stimulation. Untransduced cells were used as a negative control. The results are shown in FIGS. 2A-2R. The percentage of stained cells detected in each quadrant is given above each graph. As shown in FIGS. 2A-2R, cells transduced with a recombinant expression vector in which the β chain was positioned 5' of the α chain demonstrated improved tetramer binding as compared to cells transduced with a recombinant expression vector in which the α chain was positioned 5' of the β chain. As also shown in FIGS. 2A-2R, cells transduced with a Cys-modified TCR, a LVL-modified TCR, or a LVL-Cys-modified TCR each demonstrated improved tetramer binding as compared to cells transduced with the TCR of Example 2.

Figure 3A:
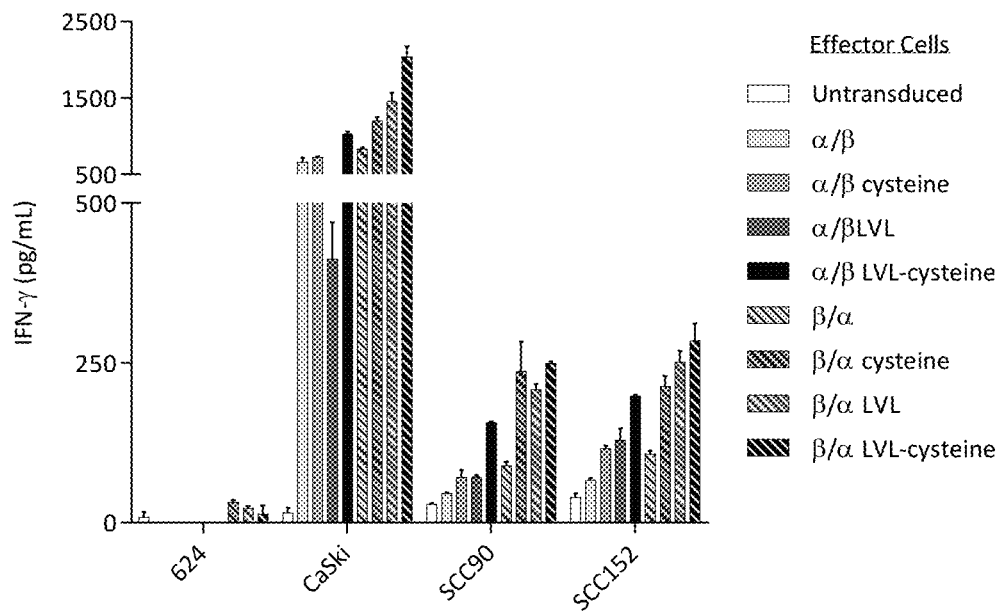
FIGS. 3A and 3B are graphs showing IFN-γ secretion by effector cells from Donor 1 (A) or Donor 2 (B) that were transduced with one of the recombinant expression vectors set forth in Table 1 upon co-culture with target 624, CaSki, SCC90, or SCC152 cells. For each target cell line, the shaded bars (from left to right) correspond to effector cells transduced with the following vector: chimeric anti-HPV 16 E7 TCR (α/β), Cys-modified TCR (α/β), LVL-modified TCR (α/β), LVL-Cys-modified TCR (α/β), chimeric anti-HPV 16 E7 TCR (β/α), Cys-modified TCR (β/α), LVL-modified TCR (β/α), or LVL-Cys-modified TCR (β/α). Untransduced cells (unshaded bars) were used as a negative control.
Figure 3B:
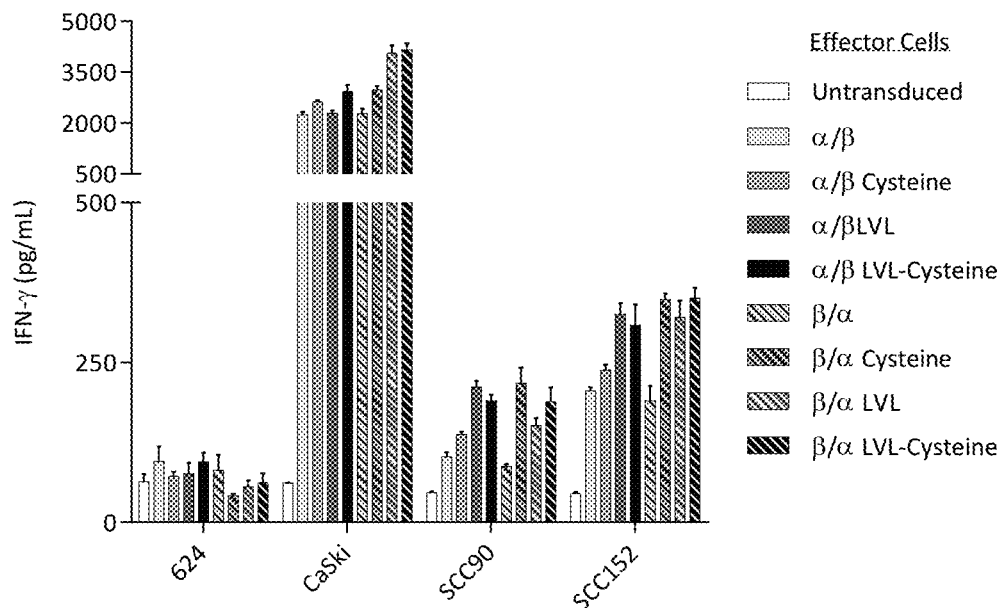

In a separate experiment, transduced cells were co-cultured with 624 cells, CaSki cells, Scc90 cells, or Scc152 cells 11 days after stimulation, and IFN-γ secretion was measured. Untransduced cells were used as a negative control. The results are shown in FIGS. 3A and 3B. As shown in FIGS. 3A and 3B, cells transduced with a Cys-modified TCR, a LVL-modified TCR, or a LVL-Cys-modified TCR each demonstrated improved recognition of HPV 16$^+$ tumor lines as compared to cells transduced with the TCR of Example 2. As also shown in FIGS. 3A-3B, cells transduced with a recombinant expression vector in which the β chain was positioned 5' of the α chain generally demonstrated improved recognition of HPV 16$^+$ tumor lines as compared to cells transduced with a recombinant expression vector in which the α chain was positioned 5' of the β chain.

Cells transduced with a recombinant expression vector in which the β chain was positioned 5' of the α chain also demonstrated improved expression as compared to cells transduced with a recombinant expression vector in which the α chain was positioned 5' of the β chain, as measured by flow cytometry.

Example 6

This example demonstrates that T cells transduced with a recombinant expression vector encoding the LVL-Cys-modified TCR (β/α) demonstrated CD8-independent binding of HPV-16 E7$_{11-19}$ tetramer.

Peripheral blood cells were transduced with the MSGV1 recombinant expression vector encoding the LVL-Cys-modified TCR (β/α) of Example 4. The transduced cells were labeled with anti-CD8, anti-TRBC (mouse constant region) antibodies, and HLA-A2/E7$_{11-19}$ tetramer and analyzed by flow cytometry. The CD8$^+$ transduced cells and the CD8$^-$ transduced cells from both donors both bound the tetramer, which demonstrated CD8-independent binding.

Example 7

This example demonstrates that peripheral blood T cells transduced to express the LVL-modified TCR (β/α) specifically recognize HPV 16 E7$_{11-19}$ peptide and HPV 16$^+$ tumor cell lines.

Figure 4:
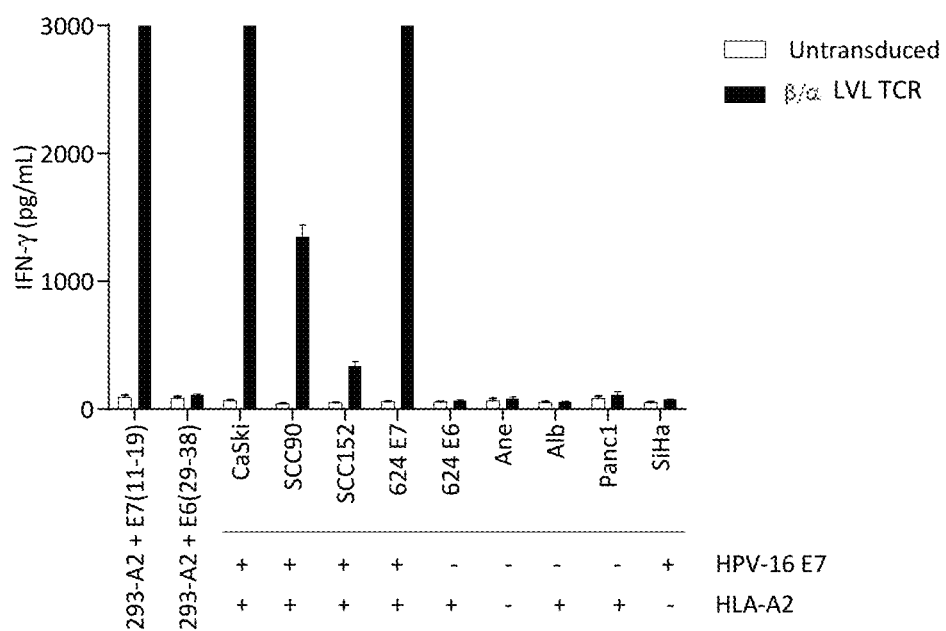
FIG. 4 is a graph showing IFN-γ (pg/mL) secreted by PBL that were transduced with a retroviral vector encoding the LVL-modified TCR (β/α) (SEQ ID NO: 37) (shaded bars) upon co-culture with target 293-A2 cells pulsed with HPV 16 E6$_{29\text{-}38}$ peptide, 293-A2 cells pulsed with HPV 16 E7$_{11\text{-}19}$ peptide, 624 cells transduced with a plasmid encoding HPV 16 E6, 624 cells transduced with a plasmid encoding HPV 16 E7, SCC152 cells, SCC90 cells, CaSki cells, Ane cells, Alb cells, Pancl cells, or SiHa cells. HLA-A2 and HPV-16 E7 expression by each target cell is indicated in the bottom of FIG. 4 ("+" indicates positive for expression and "−" indicates negative for expression). Untransduced cells (unshaded bars) were used as a negative control.

PBL were transduced with a recombinant expression vector encoding the LVL-modified TCR (β/α) (SEQ ID NO: 37) of Example 3. Rapid expansion of the numbers of cells was performed using the Rapid Expansion Protocol (REP) as previously described (Dudley et al. *J. Immunother.* 26:332-42 (2003) and Riddell et al. *J. Immunol. Methods* 128:189-201 (1990)). Briefly, TIL were cultured with irradiated (40 Gy) allogeneic peripheral blood mononuclear "feeder" cells in complete medium (CM) with 30 ng/mL anti-CD3 antibody and 6000 IU/mL IL-2. The expanded, transduced cells were co-cultured with target 293-A2 cells pulsed with HPV 16 E6$_{29-38}$ peptide (control), 293-A2 cells pulsed with HPV 16 E7$_{11-19}$ peptide, 624 cells transduced with a plasmid encoding HPV 16 E6, 624 cells transduced with a plasmid encoding HPV 16 E7, SCC152 cells, SCC90 cells, CaSki cells, Alb cells, Pancl cells, Ane cells or SiHa cells. IFN-γ was measured. The results are shown in FIG. 4. As shown in FIG. 4, PBL transduced with a recombinant expression vector encoding the LVL-modified TCR (β/α) specifically recognized HPV 16 E7-positive tumor cell lines and other HLA-A2$^+$HPV16 E7$^+$ targets in an HLA-A2-restricted manner. Results obtained with the cells of a second donor were similar.

Example 8

This example demonstrates that peripheral blood T cells transduced to express the LVL-Cys-modified TCR (β/α) specifically recognize HPV 16$^+$ tumor cell lines and that this recognition is blocked by anti-MHC Class I antibodies. This example also demonstrates these transduced T cells specifically kill HPV 16$^+$HLA-A2$^+$ tumor cell lines.

Figure 5:
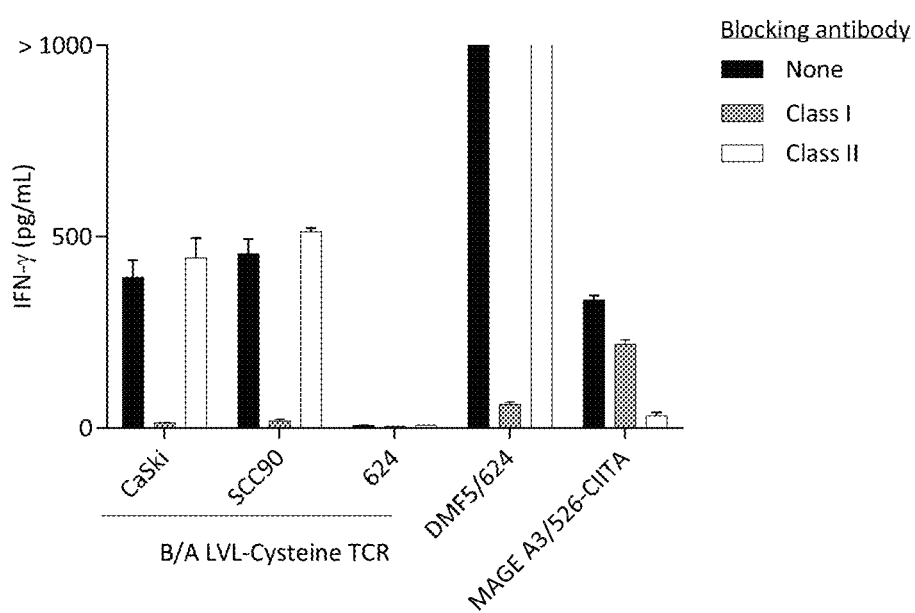
FIG. 5 is a graph showing IFN-γ (pg/mL) secreted by PBL that were transduced with a retroviral vector encoding the LVL-Cys-modified TCR (β/α) (SEQ ID NO: 38) upon co-culture with target 624 cells, SCC90 cells, or CaSki cells without antibodies (black bars) or in the presence of anti-MHC Class I (grey bars) or anti-MHC Class II antibodies (unshaded bars). As controls, PBL were transduced with DMFS TCR and co-cultured with 624 cells or transduced with anti-MAGE A3 TCR and co-cultured with 526-CIITA cells without antibodies or in the presence of anti-MHC Class I or anti-MHC Class II antibodies.
Figures 6A, 6B, 6C, 6D:
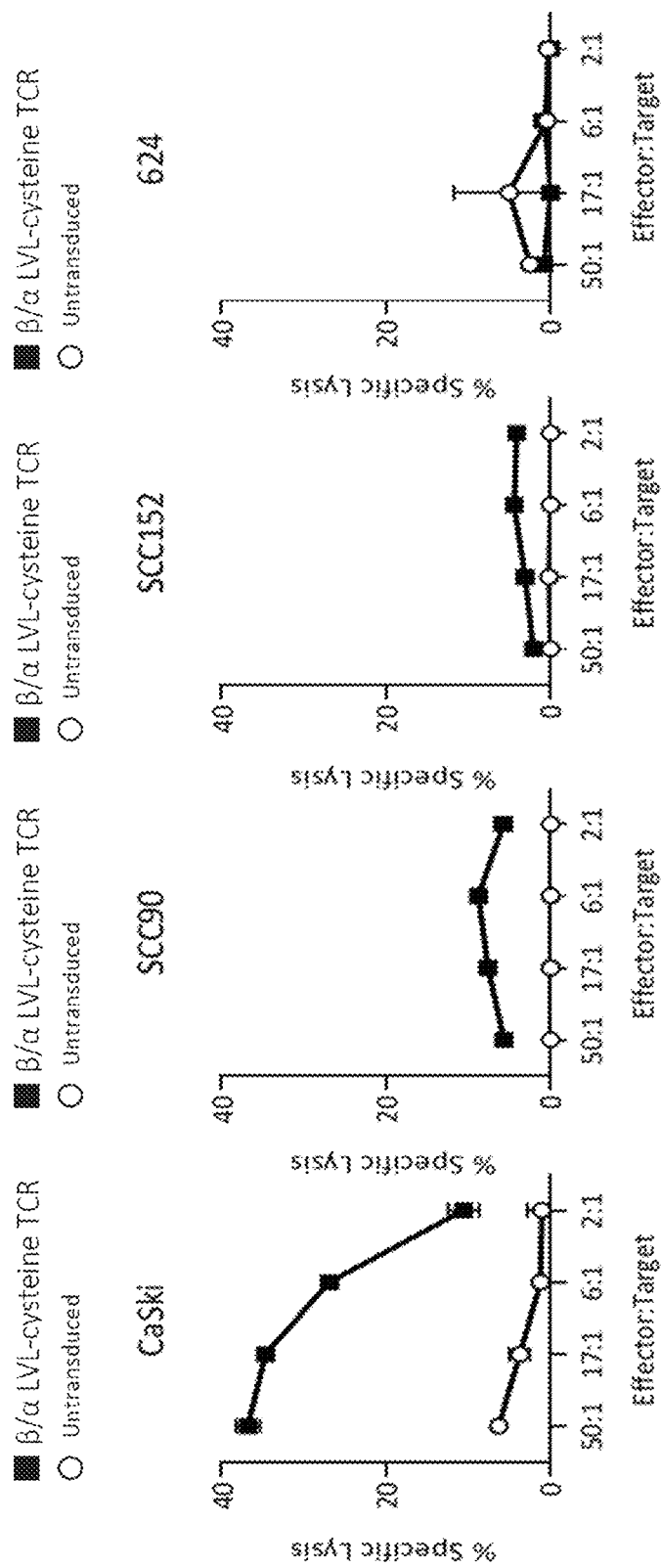
FIGS. 6A-6D are graphs showing specific lysis (%) of target cells CaSki (A), SCC90 (B), SCC152 (C), or 624 cells (D) co-cultured with effector cells transduced with a retroviral vector encoding the LVL-Cys-modified TCR (β/α) (SEQ ID NO: 38) (squares) at various effector:target ratios. Untransduced cells (circles) were used as a negative control.

PBL were transduced with a recombinant expression vector encoding the LVL-Cys-modified TCR (β/α) (SEQ ID NO: 38). Rapid expansion of the numbers of cells was performed using REP as described in Example 7. Transduced cells were co-cultured with target 624 cells, SCC90 cells, or CaSki cells without antibodies (black bars) or in the presence of anti-MHC Class I (grey bars) or anti-MHC Class II antibodies (unshaded bars). As controls, PBL were transduced with DMFS TCR and co-cultured with 624 cells or transduced with anti-MAGE A3 TCR and co-cultured with 526-CIITA cells without antibodies or in the presence of anti-MHC Class I or anti-MHC Class II antibodies. IFN-γ was measured. The results are shown in FIG. 5. As shown in FIG. 5, peripheral blood T cells transduced to express the LVL-Cys-modified TCR (β/α) specifically recognized HPV 16$^+$ tumor cell lines and this recognition was blocked by anti-MHC Class I antibodies.

In a separate experiment, transduced effector cells were co-cultured with target CaSki cells, SCC90 cells, SCC152 cells, or 624 cells at various effector:target ratios. Untransduced effector cells were used as a negative control. The results are shown in FIGS. 6A-6D. As shown in FIGS. 6A-6D, PBL transduced with a recombinant expression vector encoding the LVL-Cys-modified TCR (β/α) (SEQ ID NO: 38) demonstrated specific killing of HPV 16$^+$ HLA-A2$^+$ tumor lines.

Example 9

This example demonstrates that peripheral blood T cells transduced to express the LVL-Cys-modified TCR (β/α) have functional avidity similar to the anti-HPV 16 E6 TCR DCA2E6. This example also demonstrates that peripheral blood T cells transduced to express the LVL-Cys-modified TCR (β/α) demonstrated greater IFN-γ production upon co-culture with CaSki and SCC152 cells but not SCC90 cells as compared to cells transduced with the DCA2E6 TCR.

Figure 7A:
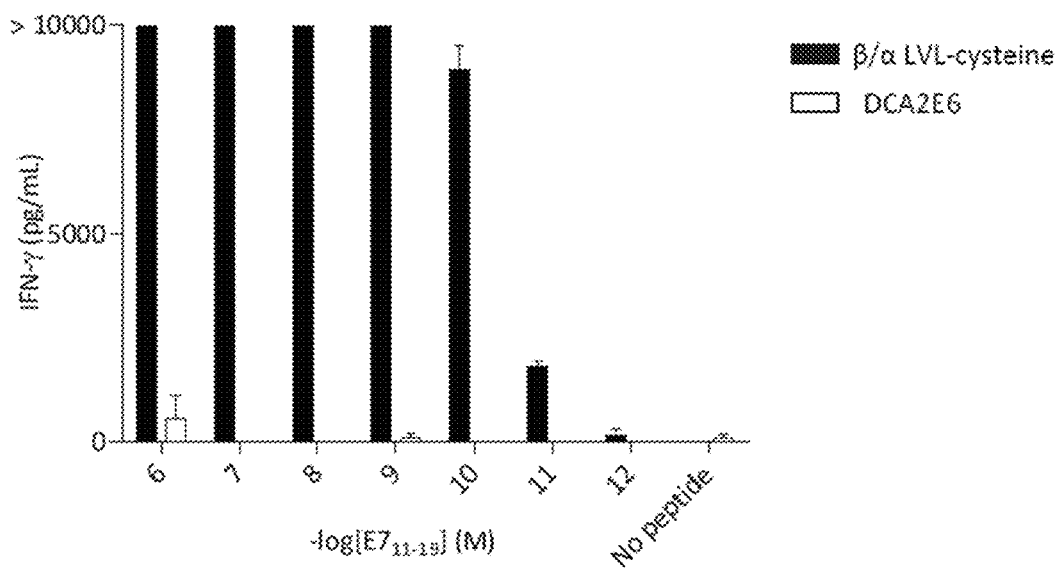
FIGS. 7A and 7B are graphs showing IFN-γ (pg/mL) secreted by PBL that were transduced with a retroviral vector encoding the LVL-Cys-modified TCR (β/α) (SEQ ID NO: 38) (shaded bars) or the anti-HPV 16 E6 TCR DCA2E6 (unshaded bars) upon co-culture with target cells pulsed with various concentrations of HPV 16 E7$_{11\text{-}19}$ peptide (A) or HPV 16 E6$_{29\text{-}38}$ peptide (B).
Figure 7B:
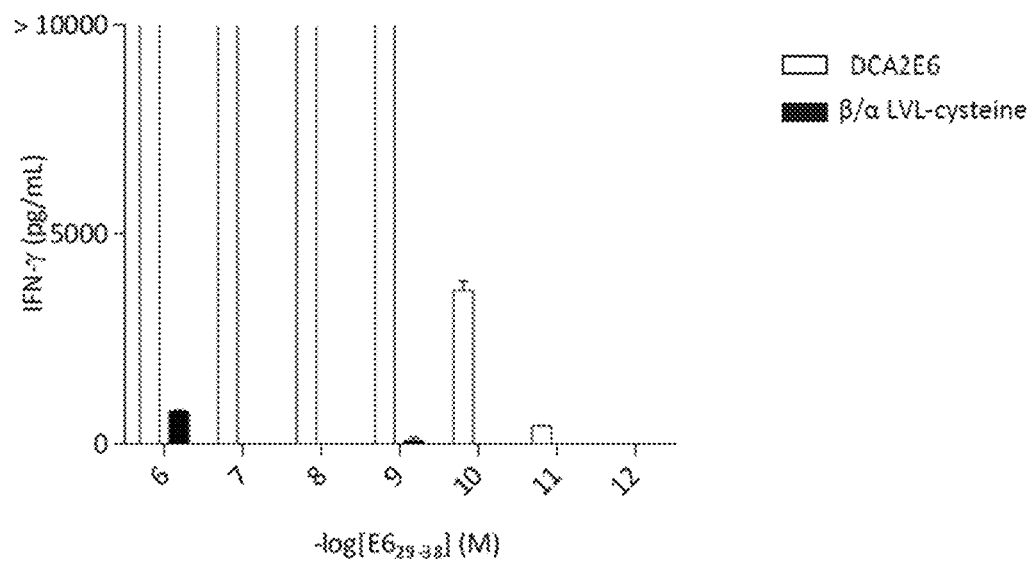

PBL were transduced with a recombinant expression vector encoding the LVL-Cys-modified TCR (β/α) (SEQ ID NO: 38) or DCA2E6. Transduced cells were co-cultured with T2 cells pulsed with no peptide or concentrations of HPV 16 E7$_{11-19}$ peptide or HPV 16 E6$_{29-38}$ peptide ranging from 1 μM to 1 pM. IFN-γ was measured. The results are shown in FIGS. 7A and 7B. As shown in FIGS. 7A and 7B, PBL transduced to express the LVL-Cys-modified TCR (β/α) have functional avidity similar to the anti-HPV 16 E6 TCR DCA2E6. Results obtained with the cells from a second donor were similar.

Figure 8A:
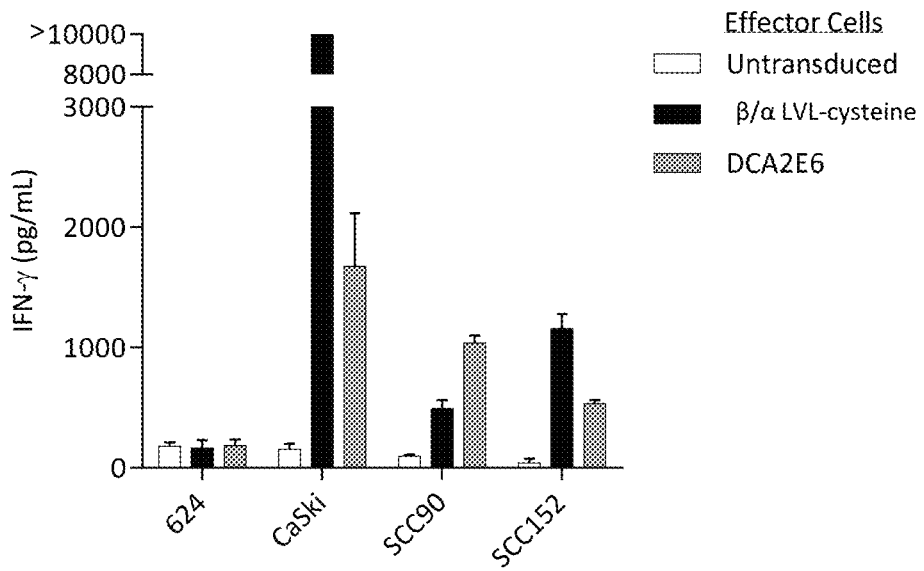
FIG. 8A is a graph showing IFN-γ (pg/mL) secreted by PBL that were transduced with a retroviral vector encoding the LVL-Cys-modified TCR (β/α) (SEQ ID NO: 38) (black bars) or the DCA2E6 TCR (grey bars) upon co-culture with target 624 cells, Caski cells, SCC90 cells, or SCC152 cells. Untransduced cells (unshaded bars) were used as a negative control.

In a separate experiment, PBL were transduced to express the LVL-Cys-modified TCR (β/α) (SEQ ID NO: 38) or DCA2E6. Untransduced cells were used as a negative control. Cells were co-cultured with target 624 cells, Caski cells, SCC90 cells, or SCC152 cells. IFN-γ was measured. The results are shown in FIG. 8A. As shown in FIG. 8A, peripheral blood T cells transduced to express the LVL-Cys-modified TCR (β/α) demonstrated greater IFN-γ production upon co-culture with CaSki and SCC152 cells but not SCC90 cells as compared to cells transduced with the DCA2E6 TCR.

Figure 8B:
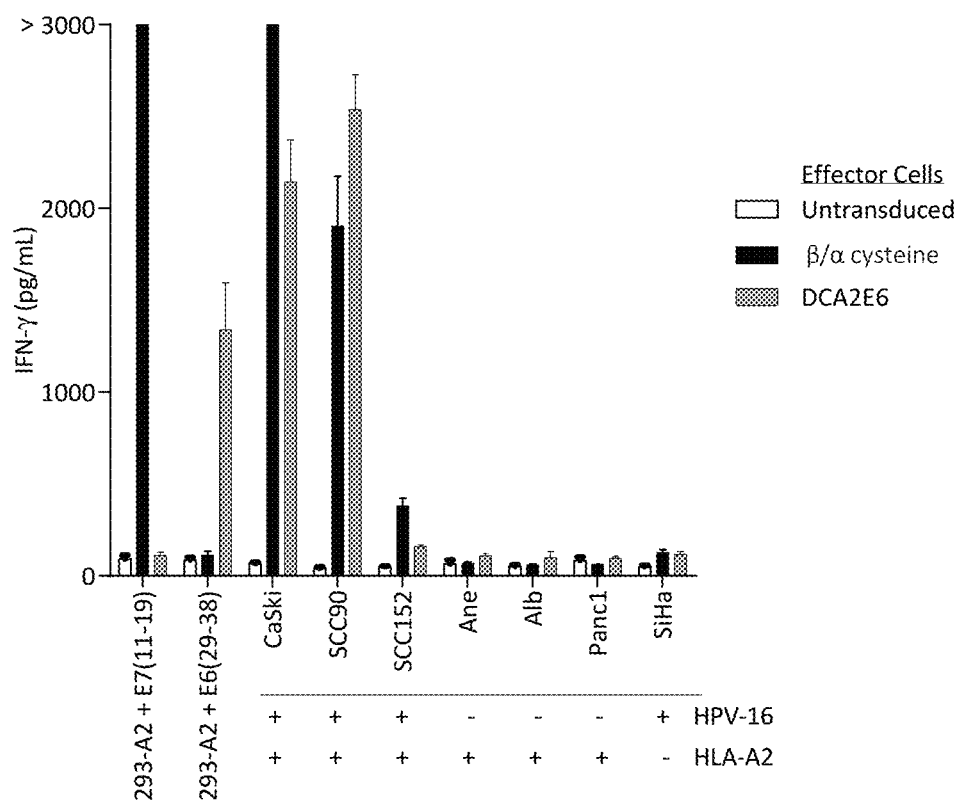
FIG. 8B is a graph showing IFN-γ (pg/mL) secreted by PBL that were transduced with a retroviral vector encoding the Cys-modified TCR (β/α) (black bars) or the DCA2E6 TCR (grey bars) upon co-culture with target 293-A2 cells pulsed with HPV 16 E629-38 peptide, 293-A2 cells pulsed with HPV 16 E7$_{11\text{-}19}$ peptide, SCC152 cells, SCC90 cells, CaSki cells, Ane cells, Alb cells, Pancl cells, or SiHa cells. Untransduced cells (unshaded bars) were used as a negative control.

In a separate experiment, PBL were transduced to express the Cys-modified TCR (β/α) (SEQ ID NOs: 9, 24, and 27) or DCA2E6. Untransduced cells were used as a negative control. Cells were co-cultured with target 293-A2 cells pulsed with HPV 16 E6$_{29-38}$ peptide (control), 293-A2 cells pulsed with HPV 16 E7$_{11-19}$ peptide, SCC152 cells, SCC90 cells, CaSki cells, Alb cells, Ane cells, Pancl cells, or SiHa cells. IFN-γ was measured. The results are shown in FIG. 8B. As shown in FIG. 8B, peripheral blood T cells transduced to express the Cys-modified TCR (β/α) demonstrated greater IFN-γ production upon co-culture with CaSki and SCC152 cells but not SCC90 cells as compared to cells transduced with the DCA2E6 TCR.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating or preventing a condition in a mammal, the method comprising administering to the mammal a population of host cells comprising a recombinant expression vector comprising a nucleic acid comprising a nucleotide sequence encoding a T cell receptor (TCR) having antigenic specificity for human papillomavirus (HPV) 16 E7, wherein the TCR comprises the amino acid sequences of SEQ ID NOs: 3-8, wherein the condition is cancer, HPV 16 infection, or HPV-positive premalignancy, and wherein the population comprises one or both of (i) cells that are allogeneic to the mammal and (ii) cells that are autologous to the mammal.

2. The method of claim 1, wherein the TCR comprises (i) a human variable region and a murine constant region or (ii) a human constant region.

3. The method of claim 1, wherein the TCR has antigenic specificity for HPV 16 E7$_{11-19}$ SEQ ID NO: 2.

4. The method of claim 1, wherein the TCR comprises the amino acid sequences of:
    (a) SEQ ID NO: 9 and
    (b) SEQ ID NO: 10, wherein X at position 2 is Ala or Gly.

5. The method of claim 1, wherein the TCR comprises the amino acid sequences of:
    (a) SEQ ID NO: 16, wherein
        (i) X at position 48 is Thr or Cys;
        (ii) X at position 112 is Ser, Gly, Ala, Val, Leu, Ile, Pro, Phe, Met, or Trp;
        (iii) X at position 114 is Met, Gly, Ala, Val, Leu, Ile, Pro, Phe, Met, or Trp; and
        (iv) X at position 115 is Gly, Ala, Val, Leu, Ile, Pro, Phe, Met, or Trp; and
    (b) SEQ ID NO: 18, wherein X at position 56 is Ser or Cys.

6. The method of claim 1, wherein the TCR comprises the amino acid sequences of:
    (a) any one of SEQ ID NOs: 14, 17, 21, 24, and 25; and
    (b) any one of SEQ ID NOs: 15, 19, and 23.

7. The method of claim 1, wherein the TCR comprises the amino acid sequences of:
    (a) (i) SEQ ID NO: 12, (ii) SEQ ID NO: 22, (iii) SEQ ID NO: 26, (iv) SEQ ID NO: 9 and 24, (v) SEQ ID NO: 9 and 16, or (vi) SEQ ID NOs: 9 and 17; and
    (b) (i) SEQ ID NOs: 10 and 18 or (ii) any one of SEQ ID NOs: 13, 20, and 27.

8. A method of treating or preventing a condition in a mammal, the method comprising administering to the mammal a population of host cells comprising a recombinant expression vector comprising a nucleic acid comprising a nucleotide sequence encoding a polypeptide comprising the amino acid sequences of SEQ ID NOs: 3-8, wherein the condition is cancer, HPV 16 infection, or HPV-positive premalignancy, and wherein the population comprises one or both of (i) cells that are allogeneic to the mammal and (ii) cells that are autologous to the mammal.

9. The method of claim 8, wherein the polypeptide comprises the amino acid sequence of SEQ ID NOs: 9 and 10, wherein X at position 2 of SEQ ID NO: 10 is Ala or Gly.

10. The method of claim 8, wherein the polypeptide comprises the amino acid sequence of:
    (a) any one of SEQ ID NOs: 29 and 30;
    (b) SEQ ID NOs: 12 and 13;
    (c) SEQ ID NOs: 20 and 22;
    (d) SEQ ID NOs: 26 and 27;
    (e) SEQ ID NOs: 9, 24, and 27;
    (f) SEQ ID NOs: 9, 17, and 20; or
    (g) SEQ ID NOs: 9, 10, 16, and 18.

11. A method of treating or preventing a condition in a mammal, the method comprising administering to the mammal a population of host cells comprising a recombinant expression vector comprising a nucleotide sequence encoding a protein comprising a first polypeptide chain comprising the amino acid sequences of SEQ ID NOs: 3-5 and a second polypeptide chain comprising the amino acid sequences of SEQ ID NOs: 6-8, wherein the condition is cancer, HPV 16 infection, or HPV-positive premalignancy, and wherein the population comprises one or both of (i) cells that are allogeneic to the mammal and (ii) cells that are autologous to the mammal.

12. The method of claim 11, wherein the nucleotide sequence encodes a first polypeptide chain comprising the amino acid sequence of SEQ ID NO: 9 and a second polypeptide chain comprising the amino acid sequence of SEQ ID NO: 10, wherein X at position 2 of SEQ ID NO: 10 is Ala or Gly.

13. The method of claim 11, wherein the nucleotide sequence encodes:
    a first polypeptide chain comprising the amino acid sequence of (i) SEQ ID NO: 12, (ii) SEQ ID NO: 22, (iii) SEQ ID NO: 26, (iv) SEQ ID NO: 9 and 16, (v) SEQ ID NO: 9 and 17, or (vi) SEQ ID NO: 9 and 24 and
    a second polypeptide chain comprising the amino acid sequence of (i) SEQ ID NO: 10 and 18, or (ii) any one of SEQ ID NOs: 13, 20, and 27.

14. The method of claim 1 comprising the nucleotide sequence of (a) SEQ ID NO: 31, (b) SEQ ID NO: 32, (c) both SEQ ID NOs: 31 and 32, (d) any one of SEQ ID NOs: 33-36, (e) both SEQ ID NOs: 33 and 34, or (f) both SEQ ID NOs: 35 and 36.

15. The method of claim 1, wherein the nucleotide sequence encodes an alpha chain and a beta chain, and the nucleotide sequence encoding the beta chain is positioned 5' of the nucleotide sequence encoding the alpha chain.

16. The method of claim 1, wherein the recombinant expression vector comprises SEQ ID NO: 37, 38, 39, or 40.

17. The method of claim 1, wherein the host cells are human.

18. The method of claim 1, comprising administering a pharmaceutical composition comprising the population of host cells and a pharmaceutically acceptable carrier.

19. The method of claim 1, wherein the condition is cancer of the uterine cervix, oropharynx, anus, anal canal, anorectum, vagina, vulva, or penis.

20. The method of claim 1, wherein the condition is an HPV 16-positive cancer.

\* \* \* \* \*

SEQUENCE LISTING

```
<160> NUMBER OF SEQ ID NOS: 40

<210> SEQ ID NO 1
<211> LENGTH: 98
<212> TYPE: PRT
<213> ORGANISM: Artificial Sequence
<220> FEATURE:
<223> OTHER INFORMATION: Synthetic

<400> SEQUENCE: 1

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Tyr Met Leu Asp Leu Gln Pro Glu Thr
1               5

<210> SEQ ID NO 3
<211> LENGTH: 6
<212> TYPE: PRT
<213> ORGANISM: Artificial Sequence
```

```
<220> FEATURE:
<223> OTHER INFORMATION: Synthetic

<400> SEQUENCE: 3

Thr Ser Gly Phe Asn Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Asn Val Leu Asp Gly Leu
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic

<400> SEQUENCE: 5

Ala Ser Val Asp Gly Asn Asn Arg Leu Ala
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Ser Gly His Asp Thr
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic

<400> SEQUENCE: 7

Tyr Tyr Glu Glu Glu Glu
1               5

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Ala Ser Ser Leu Gly Trp Arg Gly Gly Arg Tyr Asn Glu Gln Phe
1               5                   10                  15

<210> SEQ ID NO 9
<211> LENGTH: 126
<212> TYPE: PRT
<213> ORGANISM: Artificial Sequence
<220> FEATURE:
```

<223> OTHER INFORMATION: Synthetic

<400> SEQUENCE: 9

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Ser Val Asp Gly Asn Asn
            100                 105                 110

Arg Leu Ala Phe Gly Lys Gly Asn Gln Val Val Val Ile Pro
        115                 120                 125

<210> SEQ ID NO 10
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Ala or Gly

<400> SEQUENCE: 10

Met Xaa Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Gly Trp Arg Gly Gly Arg Tyr Asn Glu Gln Phe Phe Gly Pro
        115                 120                 125

Gly Thr Arg Leu Thr Val Leu
        130                 135

<210> SEQ ID NO 11
<211> LENGTH: 135
<212> TYPE: PRT
<213> ORGANISM: Artificial Sequence
<220> FEATURE:
<223> OTHER INFORMATION: Synthetic

<400> SEQUENCE: 11

Met Gly Pro Gly Leu Leu Cys Trp Ala Leu Leu Cys Leu Leu Gly Ala
1               5                   10                  15
Gly Leu Val Asp Ala Gly Val Thr Gln Ser Pro Thr His Leu Ile Lys
            20                  25                  30
Thr Arg Gly Gln Gln Val Thr Leu Arg Cys Ser Pro Lys Ser Gly His
        35                  40                  45
Asp Thr Val Ser Trp Tyr Gln Gln Ala Leu Gly Gln Gly Pro Gln Phe
    50                  55                  60
Ile Phe Gln Tyr Tyr Glu Glu Glu Arg Gln Arg Gly Asn Phe Pro
65                  70                  75                  80
Asp Arg Phe Ser Gly His Gln Phe Pro Asn Tyr Ser Ser Glu Leu Asn
                85                  90                  95
Val Asn Ala Leu Leu Leu Gly Asp Ser Ala Leu Tyr Leu Cys Ala Ser
            100                 105                 110
Ser Leu Gly Trp Arg Gly Gly Arg Tyr Asn Glu Gln Phe Phe Gly Pro
        115                 120                 125
Gly Thr Arg Leu Thr Val Leu
    130                 135

<210> SEQ ID NO 12
<211> LENGTH: 267
<212> TYPE: PRT
<213> ORGANISM: Artificial Sequence
<220> FEATURE:
<223> OTHER INFORMATION: Synthetic

<400> SEQUENCE: 12

Met Trp Gly Val Phe Leu Leu Tyr Val Ser Met Lys Met Gly Gly Thr
1               5                   10                  15
Thr Gly Gln Asn Ile Asp Gln Pro Thr Glu Met Thr Ala Thr Glu Gly
            20                  25                  30
Ala Ile Val Gln Ile Asn Cys Thr Tyr Gln Thr Ser Gly Phe Asn Gly
        35                  40                  45
Leu Phe Trp Tyr Gln Gln His Ala Gly Glu Ala Pro Thr Phe Leu Ser
    50                  55                  60
Tyr Asn Val Leu Asp Gly Leu Glu Glu Lys Gly Arg Phe Ser Ser Phe
65                  70                  75                  80
Leu Ser Arg Ser Lys Gly Tyr Ser Tyr Leu Leu Leu Lys Glu Leu Gln
                85                  90                  95
Met Lys Asp Ser Ala Ser Tyr Leu Cys Ala Ser Val Asp Gly Asn Asn
            100                 105                 110
Arg Leu Ala Phe Gly Lys Gly Asn Gln Val Val Ile Pro Asn Ile
        115                 120                 125
Gln Asn Pro Asp Pro Ala Val Tyr Gln Leu Arg Asp Ser Lys Ser Ser
    130                 135                 140
Asp Lys Ser Val Cys Leu Phe Thr Asp Phe Asp Ser Gln Thr Asn Val
145                 150                 155                 160
Ser Gln Ser Lys Asp Ser Asp Val Tyr Ile Thr Asp Lys Thr Val Leu
                165                 170                 175
Asp Met Arg Ser Met Asp Phe Lys Ser Asn Ser Ala Val Ala Trp Ser
            180                 185                 190
Asn Lys Ser Asp Phe Ala Cys Ala Asn Ala Phe Asn Asn Ser Ile Ile
        195                 200                 205
Pro Glu Asp Thr Phe Phe Pro Ser Pro Glu Ser Ser Cys Asp Val Lys
    210                 215                 220

-continued

Leu Val Glu Lys Ser Phe Glu Thr Asp Thr Asn Leu Asn Phe Gln Asn
225                 230                 235                 240

Leu Ser Val Ile Gly Phe Arg Ile Leu Leu Lys Val Ala Gly Phe
            245                 250                 255

Asn Leu Leu Met Thr Leu Arg Leu Trp Ser Ser
            260                 265

<210> SEQ ID NO 13
<211> LENGTH: 314
<212> TYPE: PRT
<213> ORGANISM: Artificial Sequence
<220> FEATURE:
<223> OTHER INFORMATION: Synthetic

<400> SEQUENCE: 13

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Gly Trp Arg Gly Gly Arg Tyr Asn Glu Gln Phe Phe Gly Pro
        115                 120                 125

Gly Thr Arg Leu Thr Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310

```
<210> SEQ ID NO 14
<211> LENGTH: 141
<212> TYPE: PRT
<213> ORGANISM: Artificial Sequence
<220> FEATURE:
<223> OTHER INFORMATION: Synthetic

<400> SEQUENCE: 14

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
        50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
        130                 135                 140

<210> SEQ ID NO 15
<211> LENGTH: 179
<212> TYPE: PRT
<213> ORGANISM: Artificial Sequence
<220> FEATURE:
<223> OTHER INFORMATION: Synthetic

<400> SEQUENCE: 15

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175
```

-continued

Ser Arg Gly

<210> SEQ ID NO 16
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (48)..(48)
<223> OTHER INFORMATION: Xaa is Thr or Cys
<220> FEATURE:
<221> NAME/KEY: MISC_FEATURE
<222> LOCATION: (112)..(112)
<223> OTHER INFORMATION: Xaa is Ser, Gly, Ala, Val, Leu, Ile, Pro, Phe,
      Met, or Trp
<220> FEATURE:
<221> NAME/KEY: MISC_FEATURE
<222> LOCATION: (114)..(114)
<223> OTHER INFORMATION: Xaa is Met, Gly, Ala, Val, Leu, Ile, Pro, Phe,
      Met, or Trp
<220> FEATURE:
<221> NAME/KEY: MISC_FEATURE
<222> LOCATION: (115)..(115)
<223> OTHER INFORMATION: Xaa is Gly, Ala, Val, Leu, Ile, Pro, Phe, Met,
      or Trp

<400> SEQUENCE: 16

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
                20                  25                  30

Asn Val Pro Lys Thr Met Glu Ser Gly Thr Phe Ile Thr Asp Lys Xaa
            35                  40                  45

Val Leu Asp Met Lys Ala Met Asp Ser Lys Ser Asn Gly Ala Ile Ala
        50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Xaa
                100                 105                 110

Val Xaa Xaa Leu Arg Ile Leu Leu Leu Lys Val Ala Gly Phe Asn Leu
            115                 120                 125

Leu Met Thr Leu Arg Leu Trp Ser Ser
        130                 135

<210> SEQ ID NO 17
<211> LENGTH: 137
<212> TYPE: PRT
<213> ORGANISM: Artificial Sequence
<220> FEATURE:
<223> OTHER INFORMATION: Synthetic

<400> SEQUENCE: 17

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
                20                  25                  30

Asn Val Pro Lys Thr Met Glu Ser Gly Thr Phe Ile Thr Asp Lys Thr
            35                  40                  45

Val Leu Asp Met Lys Ala Met Asp Ser Lys Ser Asn Gly Ala Ile Ala

```
              50                  55                  60
Trp Ser Asn Gln Thr Ser Phe Thr Cys Gln Asp Ile Phe Lys Glu Thr
 65                  70                  75                  80

Asn Ala Thr Tyr Pro Ser Ser Asp Val Pro Cys Asp Ala Thr Leu Thr
                 85                  90                  95

Glu Lys Ser Phe Glu Thr Asp Met Asn Leu Asn Phe Gln Asn Leu Ser
                100                 105                 110

Val Met Gly Leu Arg Ile Leu Leu Lys Val Ala Gly Phe Asn Leu
            115                 120                 125

Leu Met Thr Leu Arg Leu Trp Ser Ser
            130                 135

<210> SEQ ID NO 18
<211> LENGTH: 173
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (57)..(57)
<223> OTHER INFORMATION: Xaa is Ser or Cys

<400> SEQUENCE: 18

Glu Asp Leu Arg Asn Val Thr Pro Pro Lys Val Ser Leu Phe Glu Pro
  1               5                  10                  15

Ser Lys Ala Glu Ile Ala Asn Lys Gln Lys Ala Thr Leu Val Cys Leu
                 20                  25                  30

Ala Arg Gly Phe Phe Pro Asp His Val Glu Leu Ser Trp Trp Val Asn
                 35                  40                  45

Gly Lys Glu Val His Ser Gly Val Xaa Thr Asp Pro Gln Ala Tyr Lys
             50                  55                  60

Glu Ser Asn Tyr Ser Tyr Cys Leu Ser Ser Arg Leu Arg Val Ser Ala
 65                  70                  75                  80

Thr Phe Trp His Asn Pro Arg Asn His Phe Arg Cys Gln Val Gln Phe
                 85                  90                  95

His Gly Leu Ser Glu Glu Asp Lys Trp Pro Glu Gly Ser Pro Lys Pro
                100                 105                 110

Val Thr Gln Asn Ile Ser Ala Glu Ala Trp Gly Arg Ala Asp Cys Gly
            115                 120                 125

Ile Thr Ser Ala Ser Tyr Gln Gln Gly Val Leu Ser Ala Thr Ile Leu
        130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 19
<211> LENGTH: 173
<212> TYPE: PRT
<213> ORGANISM: Artificial Sequence
<220> FEATURE:
<223> OTHER INFORMATION: Synthetic

<400> SEQUENCE: 19

Glu Asp Leu Arg Asn Val Thr Pro Pro Lys Val Ser Leu Phe Glu Pro
  1               5                  10                  15

Ser Lys Ala Glu Ile Ala Asn Lys Gln Lys Ala Thr Leu Val Cys Leu
                 20                  25                  30
```

Ala Arg Gly Phe Phe Pro Asp His Val Glu Leu Ser Trp Trp Val Asn
         35                  40                  45

Gly Lys Glu Val His Ser Gly Val Ser Thr Asp Pro Gln Ala Tyr Lys
 50                  55                  60

Glu Ser Asn Tyr Ser Tyr Cys Leu Ser Ser Arg Leu Arg Val Ser Ala
 65                  70                  75                  80

Thr Phe Trp His Asn Pro Arg Asn His Phe Arg Cys Gln Val Gln Phe
                 85                  90                  95

His Gly Leu Ser Glu Glu Asp Lys Trp Pro Glu Gly Ser Pro Lys Pro
                100                 105                 110

Val Thr Gln Asn Ile Ser Ala Glu Ala Trp Gly Arg Ala Asp Cys Gly
                115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 20
<211> LENGTH: 308
<212> TYPE: PRT
<213> ORGANISM: Artificial Sequence
<220> FEATURE:
<223> OTHER INFORMATION: Synthetic

<400> SEQUENCE: 20

Met Ala Pro Gly Leu Leu Cys Trp Ala Leu Leu Cys Leu Leu Gly Ala
 1               5                  10                  15

Gly Leu Val Asp Ala Gly Val Thr Gln Ser Pro Thr His Leu Ile Lys
                 20                  25                  30

Thr Arg Gly Gln Gln Val Thr Leu Arg Cys Ser Pro Lys Ser Gly His
             35                  40                  45

Asp Thr Val Ser Trp Tyr Gln Gln Ala Leu Gly Gln Gly Pro Gln Phe
 50                  55                  60

Ile Phe Gln Tyr Tyr Glu Glu Glu Arg Gln Arg Gly Asn Phe Pro
 65                  70                  75                  80

Asp Arg Phe Ser Gly His Gln Phe Pro Asn Tyr Ser Ser Glu Leu Asn
                 85                  90                  95

Val Asn Ala Leu Leu Leu Gly Asp Ser Ala Leu Tyr Leu Cys Ala Ser
                100                 105                 110

Ser Leu Gly Trp Arg Gly Gly Arg Tyr Asn Glu Gln Phe Phe Gly Pro
            115                 120                 125

Gly Thr Arg Leu Thr Val Leu Glu Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Ser
                180                 185                 190

Thr Asp Pro Gln Ala Tyr Lys Glu Ser Asn Tyr Ser Tyr Cys Leu Ser
            195                 200                 205

Ser Arg Leu Arg Val Ser Ala Thr Phe Trp His Asn Pro Arg Asn His
    210                 215                 220

```
Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
            245                 250                 255

Trp Gly Arg Ala Asp Cys Gly Ile Thr Ser Ala Ser Tyr Gln Gln Gly
            260                 265                 270

Val Leu Ser Ala Thr Ile Leu Tyr Glu Ile Leu Gly Lys Ala Thr
            275                 280                 285

Leu Tyr Ala Val Leu Val Ser Thr Leu Val Val Met Ala Met Val Lys
        290                 295                 300

Arg Lys Asn Ser
305

<210> SEQ ID NO 21
<211> LENGTH: 137
<212> TYPE: PRT
<213> ORGANISM: Artificial Sequence
<220> FEATURE:
<223> OTHER INFORMATION: Synthetic

<400> SEQUENCE: 21

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
    130                 135

<210> SEQ ID NO 22
<211> LENGTH: 263
<212> TYPE: PRT
<213> ORGANISM: Artificial Sequence
<220> FEATURE:
<223> OTHER INFORMATION: Synthetic

<400> SEQUENCE: 22

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
```

```
            65                  70                  75                  80

Leu Ser Arg Ser Lys Gly Tyr Ser Tyr Leu Leu Lys Glu Leu Gln
                85                  90                  95

Met Lys Asp Ser Ala Ser Tyr Leu Cys Ala Ser Val Asp Gly Asn Asn
            100                 105                 110

Arg Leu Ala Phe Gly Lys Gly Asn Gln Val Val Ile Pro Asn Ile
            115                 120                 125

Gln Asn Pro Glu Pro Ala Val Tyr Gln Leu Lys Asp Pro Arg Ser Gln
130                 135                 140

Asp Ser Thr Leu Cys Leu Phe Thr Asp Phe Asp Ser Gln Ile Asn Val
145                 150                 155                 160

Pro Lys Thr Met Glu Ser Gly Thr Phe Ile Thr Asp Lys Thr Val Leu
                165                 170                 175

Asp Met Lys Ala Met Asp Ser Lys Ser Asn Gly Ala Ile Ala Trp Ser
            180                 185                 190

Asn Gln Thr Ser Phe Thr Cys Gln Asp Ile Phe Lys Glu Thr Asn Ala
                195                 200                 205

Thr Tyr Pro Ser Ser Asp Val Pro Cys Asp Ala Thr Leu Thr Glu Lys
            210                 215                 220

Ser Phe Glu Thr Asp Met Asn Leu Asn Phe Gln Asn Leu Leu Val Ile
225                 230                 235                 240

Val Leu Arg Ile Leu Leu Leu Lys Val Ala Gly Phe Asn Leu Leu Met
                245                 250                 255

Thr Leu Arg Leu Trp Ser Ser
            260

<210> SEQ ID NO 23
<211> LENGTH: 173
<212> TYPE: PRT
<213> ORGANISM: Artificial Sequence
<220> FEATURE:
<223> OTHER INFORMATION: Synthetic

<400> SEQUENCE: 23

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
                20                  25                  30

Ala Arg Gly Phe Phe Pro Asp His Val Glu Leu Ser Trp Trp Val Asn
            35                  40                  45

Gly Lys Glu Val His Ser Gly Val Cys Thr Asp Pro Gln Ala Tyr Lys
50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
            115                 120                 125

Ile Thr Ser Ala Ser Tyr Gln Gln Gly Val Leu Ser Ala Thr Ile Leu
            130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
```

165 170

<210> SEQ ID NO 24
<211> LENGTH: 137
<212> TYPE: PRT
<213> ORGANISM: Artificial Sequence
<220> FEATURE:
<223> OTHER INFORMATION: Synthetic

<400> SEQUENCE: 24

```
Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Lys Val Ala Gly Phe Asn Leu
        115                 120                 125

Leu Met Thr Leu Arg Leu Trp Ser Ser
    130                 135
```

<210> SEQ ID NO 25
<211> LENGTH: 137
<212> TYPE: PRT
<213> ORGANISM: Artificial Sequence
<220> FEATURE:
<223> OTHER INFORMATION: Synthetic

<400> SEQUENCE: 25

```
Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Lys Val Ala Gly Phe Asn Leu
        115                 120                 125

Leu Met Thr Leu Arg Leu Trp Ser Ser
    130                 135
```

<210> SEQ ID NO 26
<211> LENGTH: 263

```
<212> TYPE: PRT
<213> ORGANISM: Artificial Sequence
<220> FEATURE:
<223> OTHER INFORMATION: Synthetic

<400> SEQUENCE: 26

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Ser Val Asp Gly Asn Asn
            100                 105                 110

Arg Leu Ala Phe Gly Lys Gly Asn Gln Val Val Val Ile Pro Asn Ile
        115                 120                 125

Gln Asn Pro Glu Pro Ala Val Tyr Gln Leu Lys Asp Pro Arg Ser Gln
    130                 135                 140

Asp Ser Thr Leu Cys Leu Phe Thr Asp Phe Asp Ser Gln Ile Asn Val
145                 150                 155                 160

Pro Lys Thr Met Glu Ser Gly Thr Phe Ile Thr Asp Lys Cys Val Leu
                165                 170                 175

Asp Met Lys Ala Met Asp Ser Lys Ser Asn Gly Ala Ile Ala Trp Ser
            180                 185                 190

Asn Gln Thr Ser Phe Thr Cys Gln Asp Ile Phe Lys Glu Thr Asn Ala
        195                 200                 205

Thr Tyr Pro Ser Ser Asp Val Pro Cys Asp Ala Thr Leu Thr Glu Lys
    210                 215                 220

Ser Phe Glu Thr Asp Met Asn Leu Asn Phe Gln Asn Leu Leu Val Ile
225                 230                 235                 240

Val Leu Arg Ile Leu Leu Leu Lys Val Ala Gly Phe Asn Leu Leu Met
                245                 250                 255

Thr Leu Arg Leu Trp Ser Ser
            260

<210> SEQ ID NO 27
<211> LENGTH: 308
<212> TYPE: PRT
<213> ORGANISM: Artificial Sequence
<220> FEATURE:
<223> OTHER INFORMATION: Synthetic

<400> SEQUENCE: 27

Met Ala Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60
```

Ile Phe Gln Tyr Tyr Glu Glu Glu Arg Gln Arg Gly Asn Phe Pro
 65                  70                  75                  80

Asp Arg Phe Ser Gly His Gln Phe Pro Asn Tyr Ser Glu Leu Asn
                 85                  90                  95

Val Asn Ala Leu Leu Leu Gly Asp Ser Ala Leu Tyr Leu Cys Ala Ser
            100                 105                 110

Ser Leu Gly Trp Arg Gly Arg Tyr Asn Glu Gln Phe Phe Gly Pro
        115                 120                 125

Gly Thr Arg Leu Thr Val Leu Glu Asp Leu Arg Asn Val Thr Pro Pro
        130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Cys
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Thr Leu Val Val Met Ala Met Val Lys
290                 295                 300

Arg Lys Asn Ser
305

<210> SEQ ID NO 28
<211> LENGTH: 27
<212> TYPE: PRT
<213> ORGANISM: Artificial Sequence
<220> FEATURE:
<223> OTHER INFORMATION: Synthetic

<400> SEQUENCE: 28

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 29
<211> LENGTH: 598
<212> TYPE: PRT
<213> ORGANISM: Artificial Sequence
<220> FEATURE:
<223> OTHER INFORMATION: Synthetic

<400> SEQUENCE: 29

Met Ala Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys

-continued

```
                20                  25                  30
Thr Arg Gly Gln Gln Val Thr Leu Arg Cys Ser Pro Lys Ser Gly His
            35                  40                  45
Asp Thr Val Ser Trp Tyr Gln Gln Ala Leu Gly Gln Gly Pro Gln Phe
        50                  55                  60
Ile Phe Gln Tyr Tyr Glu Glu Glu Arg Gln Arg Gly Asn Phe Pro
65                  70                  75                  80
Asp Arg Phe Ser Gly His Gln Phe Pro Asn Tyr Ser Ser Glu Leu Asn
                85                  90                  95
Val Asn Ala Leu Leu Leu Gly Asp Ser Ala Leu Tyr Leu Cys Ala Ser
            100                 105                 110
Ser Leu Gly Trp Arg Gly Gly Arg Tyr Asn Glu Gln Phe Phe Gly Pro
        115                 120                 125
Gly Thr Arg Leu Thr Val Leu Glu Asp Leu Arg Asn Val Thr Pro Pro
        130                 135                 140
Lys Val Ser Leu Phe Glu Pro Ser Lys Ala Glu Ile Ala Asn Lys Gln
145                 150                 155                 160
Lys Ala Thr Leu Val Cys Leu Ala Arg Gly Phe Phe Pro Asp His Val
                165                 170                 175
Glu Leu Ser Trp Trp Val Asn Gly Lys Glu Val His Ser Gly Val Ser
            180                 185                 190
Thr Asp Pro Gln Ala Tyr Lys Glu Ser Asn Tyr Ser Tyr Cys Leu Ser
        195                 200                 205
Ser Arg Leu Arg Val Ser Ala Thr Phe Trp His Asn Pro Arg Asn His
        210                 215                 220
Phe Arg Cys Gln Val Gln Phe His Gly Leu Ser Glu Glu Asp Lys Trp
225                 230                 235                 240
Pro Glu Gly Ser Pro Lys Pro Val Thr Gln Asn Ile Ser Ala Glu Ala
                245                 250                 255
Trp Gly Arg Ala Asp Cys Gly Ile Thr Ser Ala Ser Tyr Gln Gln Gly
            260                 265                 270
Val Leu Ser Ala Thr Ile Leu Tyr Glu Ile Leu Leu Gly Lys Ala Thr
        275                 280                 285
Leu Tyr Ala Val Leu Val Ser Thr Leu Val Val Met Ala Met Val Lys
        290                 295                 300
Arg Lys Asn Ser Arg Ala Lys Arg Ser Gly Ser Gly Ala Thr Asn Phe
305                 310                 315                 320
Ser Leu Leu Lys Gln Ala Gly Asp Val Glu Glu Asn Pro Gly Pro Met
                325                 330                 335
Trp Gly Val Phe Leu Leu Tyr Val Ser Met Lys Met Gly Gly Thr Thr
            340                 345                 350
Gly Gln Asn Ile Asp Gln Pro Thr Glu Met Thr Ala Thr Glu Gly Ala
        355                 360                 365
Ile Val Gln Ile Asn Cys Thr Tyr Gln Thr Ser Gly Phe Asn Gly Leu
        370                 375                 380
Phe Trp Tyr Gln Gln His Ala Gly Glu Ala Pro Thr Phe Leu Ser Tyr
385                 390                 395                 400
Asn Val Leu Asp Gly Leu Glu Glu Lys Gly Arg Phe Ser Ser Phe Leu
                405                 410                 415
Ser Arg Ser Lys Gly Tyr Ser Tyr Leu Leu Leu Lys Glu Leu Gln Met
            420                 425                 430
Lys Asp Ser Ala Ser Tyr Leu Cys Ala Ser Val Asp Gly Asn Asn Arg
        435                 440                 445
```

-continued

Leu Ala Phe Gly Lys Gly Asn Gln Val Val Ile Pro Asn Ile Gln
    450                 455                 460

Asn Pro Glu Pro Ala Val Tyr Gln Leu Lys Asp Pro Arg Ser Gln Asp
465                 470                 475                 480

Ser Thr Leu Cys Leu Phe Thr Asp Phe Asp Ser Gln Ile Asn Val Pro
                485                 490                 495

Lys Thr Met Glu Ser Gly Thr Phe Ile Thr Asp Lys Thr Val Leu Asp
            500                 505                 510

Met Lys Ala Met Asp Ser Lys Ser Asn Gly Ala Ile Ala Trp Ser Asn
        515                 520                 525

Gln Thr Ser Phe Thr Cys Gln Asp Ile Phe Lys Glu Thr Asn Ala Thr
    530                 535                 540

Tyr Pro Ser Ser Asp Val Pro Cys Asp Ala Thr Leu Thr Glu Lys Ser
545                 550                 555                 560

Phe Glu Thr Asp Met Asn Leu Asn Phe Gln Asn Leu Leu Val Ile Val
                565                 570                 575

Leu Arg Ile Leu Leu Leu Lys Val Ala Gly Phe Asn Leu Leu Met Thr
            580                 585                 590

Leu Arg Leu Trp Ser Ser
        595

<210> SEQ ID NO 30
<211> LENGTH: 598
<212> TYPE: PRT
<213> ORGANISM: Artificial Sequence
<220> FEATURE:
<223> OTHER INFORMATION: Synthetic

<400> SEQUENCE: 30

Met Ala Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Gly Trp Arg Gly Gly Arg Tyr Asn Glu Gln Phe Phe Gly Pro
        115                 120                 125

Gly Thr Arg Leu Thr Val Leu Glu Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Cys
            180                 185                 190

Thr Asp Pro Gln Ala Tyr Lys Glu Ser Asn Tyr Ser Tyr Cys Leu Ser
        195                 200                 205

```
Ser Arg Leu Arg Val Ser Ala Thr Phe Trp His Asn Pro Arg Asn His
210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Thr Leu Val Met Ala Met Val Lys
290                 295                 300

Arg Lys Asn Ser Arg Ala Lys Arg Ser Gly Ser Gly Ala Thr Asn Phe
305                 310                 315                 320

Ser Leu Leu Lys Gln Ala Gly Asp Val Glu Glu Asn Pro Gly Pro Met
                325                 330                 335

Trp Gly Val Phe Leu Leu Tyr Val Ser Met Lys Met Gly Thr Thr
                340                 345                 350

Gly Gln Asn Ile Asp Gln Pro Thr Glu Met Thr Ala Thr Glu Gly Ala
            355                 360                 365

Ile Val Gln Ile Asn Cys Thr Tyr Gln Thr Ser Gly Phe Asn Gly Leu
370                 375                 380

Phe Trp Tyr Gln Gln His Ala Gly Glu Ala Pro Thr Phe Leu Ser Tyr
385                 390                 395                 400

Asn Val Leu Asp Gly Leu Glu Glu Lys Gly Arg Phe Ser Ser Phe Leu
                405                 410                 415

Ser Arg Ser Lys Gly Tyr Ser Tyr Leu Leu Leu Lys Glu Leu Gln Met
                420                 425                 430

Lys Asp Ser Ala Ser Tyr Leu Cys Ala Ser Val Asp Gly Asn Asn Arg
            435                 440                 445

Leu Ala Phe Gly Lys Gly Asn Gln Val Val Val Ile Pro Asn Ile Gln
450                 455                 460

Asn Pro Glu Pro Ala Val Tyr Gln Leu Lys Asp Pro Arg Ser Gln Asp
465                 470                 475                 480

Ser Thr Leu Cys Leu Phe Thr Asp Phe Asp Ser Gln Ile Asn Val Pro
                485                 490                 495

Lys Thr Met Glu Ser Gly Thr Phe Ile Thr Asp Lys Cys Val Leu Asp
                500                 505                 510

Met Lys Ala Met Asp Ser Lys Ser Asn Gly Ala Ile Ala Trp Ser Asn
            515                 520                 525

Gln Thr Ser Phe Thr Cys Gln Asp Ile Phe Lys Glu Thr Asn Ala Thr
530                 535                 540

Tyr Pro Ser Ser Asp Val Pro Cys Asp Ala Thr Leu Thr Glu Lys Ser
545                 550                 555                 560

Phe Glu Thr Asp Met Asn Leu Asn Phe Gln Asn Leu Leu Val Ile Val
                565                 570                 575

Leu Arg Ile Leu Leu Leu Lys Val Ala Gly Phe Asn Leu Leu Met Thr
                580                 585                 590

Leu Arg Leu Trp Ser Ser
            595

<210> SEQ ID NO 31
<211> LENGTH: 804
```

```
<212> TYPE: DNA
<213> ORGANISM: Artificial Sequence
<220> FEATURE:
<223> OTHER INFORMATION: Synthetic

<400> SEQUENCE: 31
atgtggggag ttttccttct ttatgtttcc atgaagatgg gaggcactac aggacaaaac    60
attgaccagc ccactgagat gacagctacg gaaggtgcca ttgtccagat caactgcacg   120
taccagacat ctgggttcaa cgggctgttc tggtaccagc aacatgctgg cgaagcaccc   180
acatttctgt cttacaatgt tctggatggt ttggaggaga aggtcgtttt tcttcattc    240 cttagtcggt ctaaagggta cagttacctc cttttgaagg agctccagat gaaagactct   300
gcctcttacc tctgtgcttc cgtagatggg aacaacagac tcgcttttgg gaaggggaac   360
caagtggtgg tcataccaaa tatccagaac cctgaccctg ccgtgtacca gctgagagac   420
tctaaatcca gtgacaagtc tgtctgccta ttcaccgatt ttgattctca acaaatgtg    480 tcacaaagta aggattctga tgtgtatatc acagacaaaa ctgtgctaga catgaggtct   540
atggacttca agagcaacag tgctgtggcc tggagcaaca aatctgactt tgcatgtgca   600
aacgccttca caacagcat tattccagaa gacaccttct tccccagccc agaaagttcc    660
tgtgatgtca agctggtcga gaaaagcttt gaaacagata cgaacctaaa ctttcaaaac   720
ctgtcagtga ttgggttccg aatcctcctc ctgaaagtgg ccgggtttaa tctgctcatg   780
acgctgcggc tgtggtccag ctga                                         804

<210> SEQ ID NO 32
<211> LENGTH: 945
<212> TYPE: DNA
<213> ORGANISM: Artificial Sequence
<220> FEATURE:
<223> OTHER INFORMATION: Synthetic

<400> SEQUENCE: 32
atgggccccg ggctcctctg ctgggcactg ctttgtctcc tgggagcagg cttagtggac    60
gctggagtca cccaaagtcc cacacacctg atcaaaacga gaggacagca agtgactctg   120
agatgctctc taagtctgg gcatgacact gtgtcctggt accaacaggc cctgggtcag   180
ggcccccagt ttatctttca gtattatgag gaggaagaga gacagagagg caacttccct   240
gatcgattct caggtcacca gttccctaac tatagctctg agctgaatgt gaacgccttg   300
ttgctggggg actcggccct ctatctctgt gccagcagct gggatggcg gggggccgt    360 tacaatgagc agttcttcgg gccagggaca cggctcaccg tgctagagga cctgaaaaac   420
gtgttcccac ccgaggtcgc tgtgtttgag ccatcagaag cagagatctc ccacacccaa   480
aaggccacac tggtgtgcct ggccacaggc ttctaccccg accacgtgga gctgagctgg   540
tgggtgaatg gaaggaggt gcacagtggg gtcagcacag acccgcagcc cctcaaggag   600
cagcccgccc tcaatgactc cagatactgc ctgagcagcc gctgagggt ctcggccacc   660 ttctggcaga accccgcaa ccacttccgc tgtcaagtcc agttctacgg gctctcggag   720
aatgacgagt ggacccagga tagggccaaa cctgtcaccc agatcgtcag cgccgaggcc   780
tggggtagag cagactgtgg cttcacctcc gagtcttacc agcaagggt cctgtctgcc   840 accatcctct atgagatctt gctagggaag gccaccttgt atgccgtgct ggtcagtgcc   900
ctcgtgctga tggccatggt caagagaaag gattccagag ctag                   945

<210> SEQ ID NO 33
```

```
<211> LENGTH: 795
<212> TYPE: DNA
<213> ORGANISM: Artificial Sequence
<220> FEATURE:
<223> OTHER INFORMATION: Synthetic

<400> SEQUENCE: 33
atgtggggtg tcttcctttt gtacgtcagc atgaagatgg aggcactac tgggcaaaac      60
atagatcagc ctaccgaaat gactgctacc gagggagcca ttgtccaaat caactgcacc    120
tatcagacta gcggcttcaa tggactcttc tggtaccaac agcatgcggg cgaagcacct    180
accttcttgt cctataatgt cttggatggt ctcgaagaga aaggcagatt ctccagtttc    240
ctcagccgga gcaagggata tcatatcttc tcctgaaag agcttcagat gaaggattct     300
gcatcctatc tctgtgcttc agtcgatggc aataaccgac tcgcctttgg aaaagggaat    360
caagtggtcg tcataccgaa tattcagaac cccgaaccag ccgtatatca gttgaaggac    420
ccaagatctc aggatagtac actctgtttg tttacggact tgactcaca aatcaacgtc     480
ccgaagacta tggaaagtgg tacgttcatc acagataaga cggttctgga catgaaggct    540
atggactcaa agagcaacgg ggcaattgct tggtccaacc agacaagctt tacctgtcag    600
gacattttta aggagactaa tgctactat ccctccagcg acgttccgtg tgatgcgact      660
cttaccgaga agtctttga gaccgatatg aatctcaact tccagaatct gctggtgatc     720
gttctgcgga tcctgcttct gaaggttgca ggattcaatc ttcttatgac tctccggctc    780
tggtcttcat gataa                                                      795

<210> SEQ ID NO 34
<211> LENGTH: 924
<212> TYPE: DNA
<213> ORGANISM: Artificial Sequence
<220> FEATURE:
<223> OTHER INFORMATION: Synthetic

<400> SEQUENCE: 34
atggccccgg ggcttttgtg ttgggccttg ctttgtttgc ttggggcagg cttggtggat      60
gctggagtca cacagtcacc cacacacctc attaaaacca ggggacaaca agtcactctg    120
cgctgcagtc ctaagtcagg ccatgacaca gtttcctggt atcaacaggc tctggggcag    180
ggccctcagt tcattttcca atattacgag gaagaggaac gccaacgcgg taatttcccc    240
gatcggttct ctgggcacca gttcccaaac tactcaagtg agttgaacgt aaatgctctc    300
ctcctcggag actccgccct ctacttgtgt gccagttctc ttggttggcg gggcggccga    360
tacaatgaac aattttttgg acctggtact cggctgaccg tgctagagga cctgcgcaac    420
gtcaccccac caaggtcag tttgtttgag ccatcaaagg cggagatcgc caacaaacag     480
aaagctacgc tcgtgtgttt ggctcgggc ttcttcccag accacgtaga actttcctgg      540
tgggtcaatg gaaaggaggt tcattccgga gtgtccactg atccccaagc gtacaaggaa    600
tccaactata gctactgtct ctcatctcgg ctccgggtga gtgcgacatt ctggcataat    660
cctcggaacc actttcgatg ccaagtgcag tttcatgggt tgagcgagga agacaagtgg    720
cccgagggca gtcctaaacc agtcactcaa aacataagcg ccgaggcatg gggtagagcc    780
gattgtggga ttactagcgc ttcataccaa caaggggtat tgagcgctac aattctttac    840
gaaattctcc tcggcaaggc gacgctctac gccgtactgg tgtctactct cgtggttatg    900
gcaatggtga acggaaaaa cagc                                             924
```

<210> SEQ ID NO 35
<211> LENGTH: 795
<212> TYPE: DNA
<213> ORGANISM: Artificial Sequence
<220> FEATURE:
<223> OTHER INFORMATION: Synthetic

<400> SEQUENCE: 35

```
atgtggggtg tcttcctttt gtacgtcagc atgaagatgg gaggcactac tgggcaaaac      60
atagatcagc ctaccgaaat gactgctacc gagggagcca ttgtccaaat caactgcacc     120
tatcagacta gcggcttcaa tggactcttc tggtaccaac agcatgcggg cgaagcacct     180
accttcttgt cctataatgt cttggatggt ctcgaagaga aaggcagatt ctccagtttc     240
ctcagccgga gcaagggata ctcatatctt ctcctgaaag agcttcagat gaaggattct     300
gcatcctatc tctgtgcttc agtcgatggc aataaccgac tcgcctttgg aaagggaat     360
caagtggtcg tcataccgaa tattcagaac cccgaaccag ccgtatatca gttgaaggac     420
ccaagatctc aggatagtac actctgtttg tttacggact tgactcaca aatcaacgtc      480
ccgaagacta tggaaagtgg tacgttcatc acagataagt gcgttctgga catgaaggct     540
atggactcaa agagcaacgg ggcaattgct tggtccaacc agacaagctt tacctgtcag     600
gacattttta aggagactaa tgctacttat ccctccagcg acgttccgtg tgatgcgact     660
cttaccgaga gtcttttga gaccgatatg aatctcaact tccagaatct gctggtgatc      720
gttctgcgga tcctgcttct gaaggttgca ggattcaatc ttcttatgac ctccggctc      780
tggtcttcat gataa                                                      795
```

<210> SEQ ID NO 36
<211> LENGTH: 924
<212> TYPE: DNA
<213> ORGANISM: Artificial Sequence
<220> FEATURE:
<223> OTHER INFORMATION: Synthetic

<400> SEQUENCE: 36

```
atggccccgg ggcttttgtg ttgggccttg cttttgtttgc ttgggcagg cttggtggat      60
gctggagtca cacagtcacc cacacacctc attaaaacca ggggacaaca agtcactctg     120
cgctgcagtc ctaagtcagg ccatgacaca gtttcctggt atcaacaggc tctggggcag     180
ggccctcagt tcattttcca atattacgag gaagaggaac gccaacgcgg taatttcccc     240
gatcggttct ctgggcacca gttcccaaac tactcaagtg agttgaacgt aaatgctctc     300
ctcctcggag actccgccct ctacttgtgt gccagttctc ttggttggcg gggcggccga     360
tacaatgaac aatttttggg acctggtact cggctgaccg tgctagagga cctgcgcaac     420
gtcaccccac caaaggtcag tttgtttgag ccatcaaagg cggagatcgc caacaaacag     480
aaagctacgc tcgtgtgttt ggctcggggc ttcttcccag accacgtaga actttcctgg     540
tgggtcaatg aaaggaggt tcattccgga gtgtgcactg atcccaagc gtacaaggaa      600
tccaactata gctactgtct ctcatctcgg ctccgggtga gtgcgacatt ctggcataat     660
cctcggaacc actttcgatg ccaagtgcag tttcatgggt tgagcgagga agacaagtgg     720
cccgagggca gtcctaaacc agtcactcaa aacataagcg ccgaggcatg gggtagagcc     780
gattgtggga ttactagcgc ttcataccaa caaggggtat tgagcgctac aattctttac     840
gaaattctcc tcggcaaggc gacgctctac gccgtactgg tgtctactct cgtggttatg     900
gcaatggtga aacggaaaaa cagc                                            924
```

<210> SEQ ID NO 37
<211> LENGTH: 7310
<212> TYPE: DNA
<213> ORGANISM: Artificial Sequence
<220> FEATURE:
<223> OTHER INFORMATION: Synthetic

<400> SEQUENCE: 37

| | | | | | |
|---|---|---|---|---|---|
| ccatggcccc | ggggcttttg | tgttgggcct | tgctttgttt | gcttggggca | ggcttggtgg | 60 |
| atgctggagt | cacacagtca | cccacacacc | tcattaaaac | caggggacaa | caagtcactc | 120 |
| tgcgctgcag | tcctaagtca | ggccatgaca | cagtttcctg | gtatcaacag | gctctggggc | 180 |
| agggccctca | gttcattttc | caatattacg | aggaagagga | acgccaacgc | ggtaatttcc | 240 |
| ccgatcggtt | ctctgggcac | cagttcccaa | actactcaag | tgagttgaac | gtaaatgctc | 300 |
| tcctcctcgg | agactccgcc | ctctacttgt | gtgccagttc | tcttggttgg | cggggcggcc | 360 |
| gatacaatga | acaattttt | ggacctggta | ctcggctgac | cgtgctagag | gacctgcgca | 420 |
| acgtcacccc | accaaaggtc | agtttgtttg | agccatcaaa | ggcggagatc | gccaacaaac | 480 |
| agaaagctac | gctcgtgtgt | ttggctcggg | gcttcttccc | agaccacgta | gaactttcct | 540 |
| ggtgggtcaa | tggaaaggag | gttcattccg | gagtgtccac | tgatcccaa | gcgtacaagg | 600 |
| aatccaacta | tagctactgt | ctctcatctc | ggctccgggt | gagtgcgaca | ttctggcata | 660 |
| atcctcggaa | ccactttcga | tgccaagtgc | agtttcatgg | gttgagcgag | gaagacaagt | 720 |
| ggcccgaggg | cagtcctaaa | ccagtcactc | aaaacataag | cgccgaggca | tggggtagag | 780 |
| ccgattgtgg | gattactagc | gcttcatacc | aacaaggggt | attgagcgct | acaattcttt | 840 |
| acgaaattct | cctcggcaag | gcgacgctct | acgccgtact | ggtgtctact | ctcgtggtta | 900 |
| tggcaatggt | gaaacggaaa | aacagcagag | ccaaaagaag | tggttctggc | gcgacgaatt | 960 |
| ttagtttgct | taagcaagcc | ggagatgtgg | aggaaaatcc | tggaccgatg | tggggtgtct | 1020 |
| tccttttgta | cgtcagcatg | aagatgggag | gcactactgg | gcaaaacata | gatcagccta | 1080 |
| ccgaaatgac | tgctaccgag | ggagccattg | tccaaatcaa | ctgcacctat | cagactagcg | 1140 |
| gcttcaatgg | actcttctgg | taccaacagc | atgcgggcga | agcacctacc | ttcttgtcct | 1200 |
| ataatgtctt | ggatggtctc | gaagagaaag | gcagattctc | cagtttcctc | agccggagca | 1260 |
| agggatactc | atatcttctc | ctgaaagagc | ttcagatgaa | ggattctgca | tcctatctct | 1320 |
| gtgcttcagt | cgatggcaat | aaccgactcg | cctttggaaa | agggaatcaa | gtggtcgtca | 1380 |
| taccgaatat | tcagaacccc | gaaccagccg | tatatcagtt | gaaggaccca | agatctcagg | 1440 |
| atagtacact | ctgtttgttt | acggactttg | actcacaaat | caacgtcccg | aagactatgg | 1500 |
| aaagtggtac | gttcatcaca | gataagacgg | ttctggacat | gaaggctatg | gactcaaaga | 1560 |
| gcaacggggc | aattgcttgg | tccaaccaga | caagctttac | ctgtcaggac | attttaagg | 1620 |
| agactaatgc | tacttatccc | tccagcgacg | ttccgtgtga | tgcgactctt | accgagaagt | 1680 |
| cttttgagac | cgatatgaat | ctcaacttcc | agaatctgct | ggtgatcgtt | ctgcggatcc | 1740 |
| tgcttctgaa | ggttgcagga | ttcaatcttc | ttatgactct | ccggctctgg | tcttcatgat | 1800 |
| aagaattctg | cagtcgacgg | taccgcgggc | ccgggatccg | ataaaataaa | agattttatt | 1860 |
| tagtctccag | aaaaagggg | gaatgaaaga | ccccacctgt | aggtttggca | agctagctta | 1920 |
| agtaacgcca | ttttgcaagg | catggaaaat | acataactga | gaatagagaa | gttcagatca | 1980 |
| aggttaggaa | cagagagaca | gcagaatatg | ggccaaacag | gatatctgtg | gtaagcagtt | 2040 |
| cctgccccgg | ctcagggcca | agaacagatg | gtccccagat | gcggtcccgc | cctcagcagt | 2100 |

```
ttctagagaa ccatcagatg tttccagggt gccccaagga cctgaaaatg accctgtgcc   2160
ttatttgaac taaccaatca gttcgcttct cgcttctgtt cgcgcgcttc tgctccccga   2220
gctcaataaa agagcccaca acccctcact cggcgcgcca gtcctccgat agactgcgtc   2280
gcccgggtac ccgtgtatcc aataaaccct cttgcagttg catccgactt gtggtctcgc   2340
tgttccttgg gagggtctcc tctgagtgat tgactacccg tcagcggggg tctttcatgg   2400
gtaacagttt cttgaagttg gagaacaaca ttctgagggt aggagtcgaa tattaagtaa   2460
tcctgactca attagccact gttttgaatc cacatactcc aatactcctg aaatccatcg   2520
atggagttca ttatggacag cgcagaaaga gctggggaga attgtgaaat tgttatccgc   2580
tcacaattcc acacaacata cgagccggaa gcataaagtg taaagcctgg ggtgcctaat   2640
gagtgagcta actcacatta attgcgttgc gctcactgcc cgctttccag tcgggaaacc   2700
tgtcgtgcca gctgcattaa tgaatcggcc aacgcgcggg gagaggcggt ttgcgtattg   2760
ggcgctcttc cgcttcctcg ctcactgact cgctgcgctc ggtcgttcgg ctgcggcgag   2820
cggtatcagc tcactcaaag gcggtaatac ggttatccac agaatcaggg gataacgcag   2880
gaaagaacat gtgagcaaaa ggccagcaaa aggccaggaa ccgtaaaaag gccgcgttgc   2940
tggcgttttt ccataggctc cgcccccctg acgagcatca caaaaatcga cgctcaagtc   3000
agaggtggcg aaacccgaca ggactataaa gataccaggc gtttccccct ggaagctccc   3060
tcgtgcgctc tcctgttccg accctgccgc ttaccggata cctgtccgcc tttctccctt   3120
cgggaagcgt ggcgctttct catagctcac gctgtaggta tctcagttcg gtgtaggtcg   3180
ttcgctccaa gctgggctgt gtgcacgaac cccccgttca gcccgaccgc tgcgccttat   3240
ccggtaacta tcgtcttgag tccaacccgg taagacacga cttatcgcca ctggcagcag   3300
ccactggtaa caggattagc agagcgaggt atgtaggcgg tgctacagag ttcttgaagt   3360
ggtggcctaa ctacggctac actagaagaa cagtatttgg tatctgcgct ctgctgaagc   3420
cagttacctt cggaaaaaga gttggtagct cttgatccgg caaacaaacc accgctggta   3480
gcggtggttt ttttgtttgc aagcagcaga ttacgcgcag aaaaaaagga tctcaagaag   3540
atcctttgat cttttctacg gggtctgacg ctcagtggaa cgaaaactca cgttaaggga   3600
ttttggtcat gagattatca aaaaggatct cacctagatc cttttaaatt aaaaatgaa    3660 gttttaaatc aatctaaagt atatatgagt aaacttggtc tgacagttac caatgcttaa   3720
tcagtgaggc acctatctca gcgatctgtc tatttcgttc atccatagtt gcctgactcc   3780
ccgtcgtgta gataactacg atacgggagg gcttaccatc tggccccagt gctgcaatga   3840
taccgcgaga cccacgctca ccggctccag atttatcagc aataaaccag ccagccggaa   3900
gggccgagcg cagaagtggt cctgcaactt tatccgcctc catccagtct attaattgtt   3960
gccgggaagc tagagtaagt agttcgccag ttaatagttt cgcaacgtt gttgccattg    4020 ctacaggcat cgtggtgtca cgctcgtcgt ttggtatggc ttcattcagc tccggttccc   4080
aacgatcaag gcgagttaca tgatccccca tgttgtgcaa aaaagcggtt agctccttcg   4140
gtcctccgat cgttgtcaga agtaagttgg ccgcagtgtt atcactcatg gttatggcag   4200
cactgcataa ttctcttact gtcatgccat ccgtaagatg cttttctgtg actggtgagt   4260
actcaaccaa gtcattctga gaatagtgta tgcggcgacc gagttgctct tgcccggcgt   4320
caatacggga taataccgcg ccacatagca gaactttaaa agtgctcatc attggaaaac   4380
gttcttcggg gcgaaaactc tcaaggatct taccgctgtt gagatccagt tcgatgtaac   4440
```

```
ccactcgtgc acccaactga tcttcagcat ctttttacttt caccagcgtt tctgggtgag    4500
caaaaacagg aaggcaaaat gccgcaaaaa agggaataag ggcgacacgg aaatgttgaa    4560
tactcatact cttcctttt caatattatt gaagcattta tcagggttat tgtctcatga    4620
gcggatacat atttgaatgt atttagaaaa ataaacaaat aggggttccg cgcacatttc    4680
cccgaaaagt gccacctgac gtctaagaaa ccattattat catgacatta acctataaaa    4740
ataggcgtat cacgaggccc tttcgtctcg cgcgtttcgg tgatgacggt gaaaacctct    4800
gacacatgca gctcccggag acggtcacag cttgtctgta agcggatgcc gggagcagac    4860
aagcccgtca gggcgcgtca gcgggtgttg gcgggtgtcg gggctggctt aactatgcgg    4920
catcagagca gattgtactg agagtgcacc atatgcggtg tgaaataccg cacagatgcg    4980
taaggagaaa ataccgcatc aggcgccatt cgccattcag gctgcgcaac tgttgggaag    5040
ggcgatcggt gcgggcctct tcgctattac gccagctggc gaaaggggga tgtgctgcaa    5100
ggcgattaag ttgggtaacg ccagggtttt cccagtcacg acgttgtaaa acgacggcgc    5160
aaggaatggt gcatgcaagg agatggcgcc caacagtccc ccggccacgg ggcctgccac    5220
catacccacg ccgaaacaag cgctcatgag cccgaagtgg cgagcccgat cttccccatc    5280
ggtgatgtcg gcgatatagg cgccagcaac cgcacctgtg gcgccggtga tgccggccac    5340
gatgcgtccg gcgtagaggc gattagtcca atttgttaaa gacaggatat cagtggtcca    5400
ggctctagtt ttgactcaac aatatcacca gctgaagcct atagagtacg agccatagat    5460
aaaataaaag atttatttta gtctccagaa aaggggggga atgaaagacc ccacctgtag    5520
gtttggcaag ctagcttaag taacgccatt ttgcaaggca tggaaaatac ataactgaga    5580
atagagaagt tcagatcaag gttaggaaca gagagacagc agaatatggg ccaaacagga    5640
tatctgtggt aagcagttcc tgccccggct cagggccaag aacagatggt ccccagatgc    5700
ggtcccgccc tcagcagttt ctagagaacc atcagatgtt tccagggtgc cccaaggacc    5760
tgaaatgacc ctgtgcctta tttgaactaa ccaatcagtt cgcttctcgc ttctgttcgc    5820
gcgcttctgc tccccgagct caataaaaga gcccacaacc cctcactcgg cgcgccagtc    5880
ctccgataga ctgcgtcgcc cgggtacccg tattcccaat aaagcctctt gctgtttgca    5940
tccgaatcgt ggactcgctg atccttggga gggtcctc agattgattg actgcccacc    6000 tcggggggtct ttcatttgga ggttccaccg agatttggag acccctgccc agggaccacc    6060
gacccccccg ccgggaggta agctggccag cggtcgtttc gtgtctgtct ctgtctttgt    6120 gcgtgttttgt gccggcatct aatgtttgcg cctgcgtctg tactagttag ctaactagct    6180
ctgtatctgg cggacccgtg gtggaactga cgagttcgga acacccggcc gcaaccctgg    6240
gagacgtccc agggacttcg ggggccgttt ttgtggcccg acctgagtcc taaaatcccg    6300
atcgtttagg actctttggt gcaccccct tagaggaggg atatgtggtt ctggtaggag    6360
acgagaacct aaaacagttc ccgcctccgt ctgaattttt gctttcggtt tgggaccgaa    6420
gccgcgccgc gcgtcttgtc tgctgcagca tcgttctgtg ttgtctctgt ctgactgtgt    6480 ttctgtatttt gtctgaaaat atgggcccgg gctagcctgt taccactccc ttaagtttga    6540
ccttaggtca ctggaaagat gtcgagcgga tcgctcacaa ccagtcggta gatgtcaaga    6600
agagacgttg ggttaccttc tgctctgcag aatggccaac ctttaacgtc ggatggccgc    6660
gagacggcac ctttaaccga gacctcatca cccaggttaa gatcaaggtc ttttcacctg    6720
gcccgcatgg acacccagac caggtcccct acatcgtgac ctgggaagcc ttggcttttg    6780 accccccctcc ctgggtcaag cccttttgtac accctaagcc tccgcctcct cttcctccat    6840
```

```
ccgccccgtc tctccccctt gaacctcctc gttcgacccc gcctcgatcc tcccttatc      6900 cagccctcac tccttctcta ggcgccccca tatggccata tgagatctta tatggggcac     6960
ccccgcccct tgtaaacttc cctgaccctg acatgacaag agttactaac agccctctc      7020 tccaagctca cttacaggct ctctacttag tccagcacga agtctggaga cctctggcgg     7080
cagcctacca agaacaactg gaccgaccgg tggtacctca cccttaccga gtcggcgaca     7140
cagtgtgggt ccgccgacac cagactaaga acctagaacc tcgctggaaa ggaccttaca    7200
cagtcctgct gaccaccccc accgccctca agtagacgg catcgcagct tggatacacg      7260
ccgcccacgt gaaggctgcc gaccccgggg gtggaccatc ctctagaccg                7310

<210> SEQ ID NO 38
<211> LENGTH: 7310
<212> TYPE: DNA
<213> ORGANISM: Artificial Sequence
<220> FEATURE:
<223> OTHER INFORMATION: Synthetic

<400> SEQUENCE: 38
ccatggcccc ggggcttttg tgttgggcct tgctttgttt gcttggggca ggcttggtgg      60
atgctggagt cacacagtca cccacacacc tcattaaaac caggggacaa caagtcactc     120
tgcgctgcag tcctaagtca ggccatgaca cagtttcctg gtatcaacag gctctggggc     180
agggccctca gttcattttc caatattacg aggaagagga acgccaacgc ggtaatttcc     240
ccgatcggtt ctctgggcac cagttcccaa actactcaag tgagttgaac gtaaatgctc     300
tcctcctcgg agactccgcc ctctacttgt gtgccagttc tcttggttgg cggggcggcc     360
gatacaatga acaattttt ggacctggta ctcggctgac cgtgctagag gacctgcgca     420
acgtcacccc accaaaggtc agtttgtttg agccatcaaa ggcggagatc gccaacaaac     480
agaaagctac gctcgtgtgt ttggctcggg gcttcttccc agaccacgta gaactttcct     540
ggtgggtcaa tggaaaggag gttcattccg gagtgtgcac tgatccccaa gcgtacaagg     600
aatccaacta tagctactgt ctctcatctc ggctccgggt gagtgcgaca ttctggcata     660
atcctcggaa ccactttcga tgccaagtgc agtttcatgg gttgagcgag gaagacaagt     720
ggcccgaggg cagtcctaaa ccagtcactc aaaacataag cgccgaggca tgggtagag     780 ccgattgtgg gattactagc gcttcatacc aacaaggggt attgagcgct acaattcttt     840
acgaaattct cctcggcaag gcgacgctct acgccgtact ggtgtctact ctcgtggtta     900
tggcaatggt gaaacggaaa aacagcagag ccaaagaag tggttctggc gcgacgaatt     960
ttagtttgct taagcaagcc ggagatgtgg aggaaaatcc tggaccgatg tggggtgtct    1020
tccttttgta cgtcagcatg aagatgggag gcactactgg gcaaaacata gatcagccta    1080
ccgaaatgac tgctaccgag ggagccattg tccaaatcaa ctgcacctat cagactagcg    1140
gcttcaatgg actcttctgg taccaacagc atgcgggcga agcacctacc ttcttgtcct    1200
ataatgtctt ggatggtctc gaagagaaag gcagattctc cagtttcctc agccggagca    1260
agggatactc atatcttctc ctgaaagagc ttcagatgaa ggattctgca tcctatctct    1320
gtgcttcagt cgatggcaat aaccgactcg cctttggaaa agggaatcaa gtggtcgtca    1380
taccgaatat tcagaacccc gaaccagccg tatatcagtt gaaggaccca agatctcagg    1440
atagtacact ctgtttgttt acggactttg actcacaaat caacgtcccg aagactatgg    1500
aaagtggtac gttcatcaca gataagtgcg ttctggacat gaaggctatg gactcaaaga    1560
```

-continued

```
gcaacggggc aattgcttgg tccaaccaga caagctttac ctgtcaggac attttttaagg   1620
agactaatgc tacttatccc tccagcgacg ttccgtgtga tgcgactctt accgagaagt   1680
cttttgagac cgatatgaat ctcaacttcc agaatctgct ggtgatcgtt ctgcggatcc   1740
tgcttctgaa ggttgcagga ttcaatcttc ttatgactct ccggctctgg tcttcatgat   1800
aagaattctg cagtcgacgg taccgcgggc ccgggatccg ataaaataaa agatttttatt  1860
tagtctccag aaaaggggg gaatgaaaga ccccacctgt aggtttggca agctagctta   1920
agtaacgcca ttttgcaagg catggaaaat acataactga aatagagaa gttcagatca   1980
aggttaggaa cagagagaca gcagaatatg ggccaaacag gatatctgtg gtaagcagtt   2040
cctgccccgg ctcagggcca agaacagatg gtccccagat gcggtcccgc cctcagcagt   2100
ttctagagaa ccatcagatg tttccagggt gccccaagga cctgaaaatg accctgtgcc   2160
ttatttgaac taaccaatca gttcgcttct cgcttctgtt cgcgcgcttc tgctccccga   2220
gctcaataaa agagcccaca acccctcact cggcgcgcca gtcctccgat agactgcgtc   2280
gcccgggtac ccgtgtatcc aataaaccct cttgcagttg catccgactt gtggtctcgc   2340
tgttccttgg gagggtctcc tctgagtgat tgactacccg tcagcggggg tctttcatgg   2400
gtaacagttt cttgaagttg gagaacaaca ttctgagggt aggagtcgaa tattaagtaa   2460
tcctgactca attagccact gttttgaatc cacatactcc aatactcctg aaatccatcg   2520
atggagttca ttatggacag cgcagaaaga gctggggaga attgtgaaat tgttatccgc   2580
tcacaattcc acacaacata cgagccggaa gcataaagtg taaagcctgg ggtgcctaat   2640
gagtgagcta actcacatta attgcgttgc gctcactgcc cgctttccag tcgggaaacc   2700
tgtcgtgcca gctgcattaa tgaatcggcc aacgcgcggg gagaggcggt ttgcgtattg   2760
ggcgctcttc cgcttcctcg ctcactgact cgctgcgctc ggtcgttcgg ctgcggcgag   2820
cggtatcagc tcactcaaag gcggtaatac ggttatccac agaatcaggg gataacgcag   2880
gaaagaacat gtgagcaaaa ggccagcaaa aggccaggaa ccgtaaaaag gccgcgttgc   2940
tggcgttttt ccataggctc cgcccccctg acgagcatca caaaaatcga cgctcaagtc   3000
agaggtggcg aaacccgaca ggactataaa gataccaggc gtttccccct ggaagctccc   3060
tcgtgcgctc tcctgttccg accctgccgc ttaccggata cctgtccgcc tttctccctt   3120
cgggaagcgt ggcgctttct catagctcac gctgtaggta tctcagttcg gtgtaggtcg   3180
ttcgctccaa gctgggctgt gtgcacgaac cccccgttca gcccgaccgc tgcgccttat   3240
ccggtaacta tcgtcttgag tccaacccgg taagacacga cttatcgcca ctggcagcag   3300
ccactggtaa caggattagc agagcgaggt atgtaggcgg tgctacagag ttcttgaagt   3360
ggtggcctaa ctacggctac actagaagaa cagtatttgg tatctgcgct ctgctgaagc   3420
cagttacctt cggaaaaaga gttggtagct cttgatccgg caaacaaacc accgctggta   3480
gcggtggttt ttttgtttgc aagcagcaga ttacgcgcag aaaaaaagga tctcaagaag   3540
atcctttgat cttttctacg ggtctgacg ctcagtggaa cgaaaactca cgttaaggga   3600
ttttggtcat gagattatca aaaaggatct tcacctagat ccttttaaat taaaaatgaa   3660
gttttaaatc aatctaaagt atatatgagt aaacttggtc tgacagttac caatgcttaa   3720
tcagtgaggc acctatctca gcgatctgtc tatttcgttc atccatagtt gcctgactcc   3780
ccgtcgtgta gataactacg atacgggagg gcttaccatc tggccccagt gctgcaatga   3840
taccgcgaga cccacgctca ccggctccag atttatcagc aataaaccag ccagccgaa   3900
gggccgagcg cagaagtggt cctgcaactt tatccgcctc catccagtct attaattgtt   3960
```

```
gccgggaagc tagagtaagt agttcgccag ttaatagttt gcgcaacgtt gttgccattg    4020
ctacaggcat cgtggtgtca cgctcgtcgt ttggtatggc ttcattcagc tccggttccc    4080
aacgatcaag gcgagttaca tgatccccca tgttgtgcaa aaagcggtt agctccttcg    4140
gtcctccgat cgttgtcaga agtaagttgg ccgcagtgtt atcactcatg gttatggcag    4200
cactgcataa ttctcttact gtcatgccat ccgtaagatg cttttctgtg actggtgagt    4260
actcaaccaa gtcattctga gaatagtgta tgcggcgacc gagttgctct tgcccggcgt    4320
caatacggga taataccgcg ccacatagca gaactttaaa agtgctcatc attggaaaac    4380
gttcttcggg gcgaaaactc tcaaggatct taccgctgtt gagatccagt tcgatgtaac    4440
ccactcgtgc acccaactga tcttcagcat cttttacttt caccagcgtt tctgggtgag    4500
caaaaacagg aaggcaaaat gccgcaaaaa agggaataag ggcgacacgg aaatgttgaa    4560
tactcatact cttccttttt caatattatt gaagcattta tcagggttat tgtctcatga    4620
gcggatacat atttgaatgt atttagaaaa ataaacaaat aggggttccg cgcacatttc    4680
cccgaaaagt gccacctgac gtctaagaaa ccattattat catgacatta acctataaaa    4740
ataggcgtat cacgaggccc tttcgtctcg cgcgtttcgg tgatgacggt gaaaacctct    4800
gacacatgca gctcccggag acggtcacag cttgtctgta agcggatgcc gggagcagac    4860
aagcccgtca gggcgcgtca gcgggtgttg gcgggtgtcg gggctggctt aactatgcgg    4920
catcagagca gattgtactg agagtgcacc atatgcggtg tgaaataccg cacagatgcg    4980
taaggagaaa ataccgcatc aggcgccatt cgccattcag gctgcgcaac tgttgggaag    5040
ggcgatcggt gcgggcctct tcgctattac gccagctggc gaaaggggga tgtgctgcaa    5100
ggcgattaag ttgggtaacg ccagggtttt cccagtcacg acgttgtaaa acgacggcgc    5160
aaggaatggt gcatgcaagg agatggcgcc caacagtccc ccggccacgg ggcctgccac    5220
catacccacg ccgaaacaag cgctcatgag cccgaagtgg cgagcccgat cttccccatc    5280
ggtgatgtcg gcgatatagg cgccagcaac cgcacctgtg gcgccggtga tgccggccac    5340
gatgcgtccg gcgtagaggc gattagtcca atttgttaaa gacaggatat cagtggtcca    5400
ggctctagtt ttgactcaac aatatcacca gctgaagcct atagagtacg agccatagat    5460
aaaataaaag atttatttta gtctccagaa aagggggga atgaaagacc ccacctgtag    5520
gtttggcaag ctagcttaag taacgccatt ttgcaaggca tggaaaatac ataactgaga    5580
atagagaagt tcagatcaag gttaggaaca gagagacagc agaatatggg ccaaacagga    5640
tatctgtggt aagcagttcc tgccccggct cagggccaag aacagatggt ccccagatgc    5700
ggtcccgccc tcagcagttt ctagagaacc atcagatgtt tccagggtgc cccaaggacc    5760
tgaaatgacc ctgtgcctta tttgaactaa ccaatcagtt cgcttctcgc ttctgttcgc    5820
gcgcttctgc tccccgagct caataaaaga gcccacaacc cctcactcgg cgcgccagtc    5880
ctccgataga ctgcgtcgcc cgggtacccg tattcccaat aaagcctctt gctgtttgca    5940
tccgaatcgt ggactcgctg atccttggga gggtctcctc agattgattg actgcccacc    6000
tcggggtct ttcatttgga ggttccaccg agatttggag accctgccc agggaccacc     6060
gacccccccg ccgggaggta agctggccag cggtcgtttc gtgtctgtct ctgtctttgt    6120
gcgtgtttgt gccggcatct aatgtttgcg cctgcgtctg tactagttag ctaactagct    6180
ctgtatctgg cggaccgtg gtggaactga cgagttcgga acaccggcc gcaaccctgg      6240
gagacgtccc agggacttcg ggggccgttt ttgtggcccg acctgagtcc taaaatcccg    6300
```

```
atcgtttagg actctttggt gcaccccct tagaggaggg atatgtggtt ctggtaggag    6360
acgagaacct aaaacagttc ccgcctccgt ctgaattttt gctttcggtt tgggaccgaa    6420
gccgcgccgc gcgtcttgtc tgctgcagca tcgttctgtg ttgtctctgt ctgactgtgt    6480
ttctgtattt gtctgaaaat atgggcccgg gctagcctgt taccactccc ttaagtttga    6540
ccttaggtca ctggaaagat gtcgagcgga tcgctcacaa ccagtcggta gatgtcaaga    6600
agagacgttg ggttaccttc tgctctgcag aatggccaac ctttaacgtc ggatggccgc    6660
gagacggcac ctttaaccga gacctcatca cccaggttaa gatcaaggtc ttttcacctg    6720
gcccgcatgg acacccagac caggtcccct acatcgtgac ctgggaagcc ttggcttttg    6780
accccctcc ctgggtcaag ccctttgtac accctaagcc tccgcctcct cttcctccat    6840
ccgcccgtc tctcccctt gaacctcctc gttcgacccc gctcgatcc tcctttatc    6900
cagccctcac tccttctcta ggcgccccca tatggccata tgagatctta tatggggcac    6960
ccccgcccct tgtaaacttc cctgaccctg acatgacaag agttactaac agccctctc    7020
tccaagctca cttacaggct ctctacttag tccagcacga agtctggaga cctctggcgg    7080
cagcctacca agaacaactg gaccgaccgg tggtacctca cccttaccga gtcggcgaca    7140
cagtgtgggt ccgccgacac cagactaaga acctagaacc tcgctggaaa ggaccttaca    7200
cagtcctgct gaccaccccc accgccctca agtagacgg catcgcagct tggatacacg    7260
ccgcccacgt gaaggctgcc gaccccgggg gtggaccatc tctagaccg                7310
```

```
<210> SEQ ID NO 39
<211> LENGTH: 1800
<212> TYPE: DNA
<213> ORGANISM: Artificial Sequence
<220> FEATURE:
<223> OTHER INFORMATION: Synthetic

<400> SEQUENCE: 39
```

```
atggccccgg ggcttttgtg ttgggccttg ctttgtttgc ttggggcagg cttggtggat      60
gctggagtca cacagtcacc cacacacctc attaaaacca ggggacaaca agtcactctg     120
cgctgcagtc ctaagtcagg ccatgacaca gtttcctggt atcaacaggc tctggggcag     180
ggccctcagt tcatttttcca atattacgag gaagaggaac gccaacgcgg taatttcccc     240
gatcggttct ctgggcacca gttcccaaac tactcaagtg agttgaacgt aaatgctctc     300
ctcctcggag actccgccct ctacttgtgt gccagttctc ttggttggcg gggcggccga     360
tacaatgaac aatttttggg acctggtact cggctgaccg tgctagagga cctgcgcaac     420
gtcaccccac caaaggtcag tttgtttgag ccatcaaagg cggagatcgc caacaaacag     480
aaagctacgc tcgtgtgttt ggctcggggc ttcttcccag accacgtaga actttcctgg     540
tgggtcaatg gaaggaggt tcattccgga gtgtccactg atccccaagc gtacaaggaa     600
tccaactata gctactgtct ctcatctcgg ctccgggtga gtgcgacatt ctggcataat     660
cctcggaacc actttcgatg ccaagtgcag tttcatgggt tgagcgagga agacaagtgg     720
cccgagggca gtcctaaacc agtcactcaa acataagcg ccgaggcatg gggtagagcc     780
gattgtggga ttactagcgc ttcataccaa caagggtat tgagcgctac aattctttac     840
gaaattctcc tcggcaaggc gacgctctac gccgtactgg tgtctactct cgtggttatg     900
gcaatggtga acggaaaaaa cagcagagcc aaaagaagtg ttctggcgc gacgaatttt     960
agtttgctta agcaagccgg agatgtggag gaaaatcctg accgatgtg gggtgtcttc    1020
cttttgtacg tcagcatgaa gatgggaggc actactgggc aaaacataga tcagcctacc    1080
```

| | |
|---|---|
| gaaatgactg ctaccgaggg agccattgtc caaatcaact gcacctatca gactagcggc | 1140 |
| ttcaatggac tcttctggta ccaacagcat gcgggcgaag cacctacctt cttgtcctat | 1200 |
| aatgtcttgg atggtctcga agagaaaggc agattctcca gtttcctcag ccggagcaag | 1260 |
| ggatactcat atcttctcct gaaagagctt cagatgaagg attctgcatc ctatctctgt | 1320 |
| gcttcagtcg atggcaataa ccgactcgcc tttggaaaag ggaatcaagt ggtcgtcata | 1380 |
| ccgaatattc agaaccccga accagccgta tatcagttga aggacccaag atctcaggat | 1440 |
| agtacactct gtttgtttac ggactttgac tcacaaatca acgtcccgaa gactatggaa | 1500 |
| agtggtacgt tcatcacaga taagacggtt ctggacatga aggctatgga ctcaaagagc | 1560 |
| aacgggcaa ttgcttggtc caaccagaca agctttacct gtcaggacat ttttaaggag | 1620 |
| actaatgcta cttatccctc cagcgacgtt ccgtgtgatg cgactcttac cgagaagtct | 1680 |
| tttgagaccg atatgaatct caacttccag aatctgctgg tgatcgttct gcggatcctg | 1740 |
| cttctgaagg ttgcaggatt caatcttctt atgactctcc ggctctggtc ttcatgataa | 1800 |

<210> SEQ ID NO 40
<211> LENGTH: 1800
<212> TYPE: DNA
<213> ORGANISM: Artificial Sequence
<220> FEATURE:
<223> OTHER INFORMATION: Synthetic

<400> SEQUENCE: 40

| | |
|---|---|
| atggccccgg ggcttttgtg ttgggccttg cttttgtttgc ttggggcagg cttggtggat | 60 |
| gctggagtca cacagtcacc cacacacctc attaaaacca ggggacaaca agtcactctg | 120 |
| cgctgcagtc ctaagtcagg ccatgacaca gtttcctggt atcaacaggc tctggggcag | 180 |
| ggccctcagt tcattttcca atattacgag gaagaggaac gccaacgcgg taatttcccc | 240 |
| gatcggttct ctgggcacca gttcccaaac tactcaagtg agttgaacgt aaatgctctc | 300 |
| ctcctcggag actccgccct ctacttgtgt gccagttctc ttggttggcg gggcggccga | 360 |
| tacaatgaac aatttttttgg acctggtact cggctgaccg tgctagagga cctgcgcaac | 420 |
| gtcaccccac caaaggtcag tttgtttgag ccatcaaagg cggagatcgc caacaaacag | 480 |
| aaagctacgc tcgtgtgttt ggctcggggc ttcttcccag accacgtaga actttcctgg | 540 |
| tgggtcaatg gaaaggaggt tcattccgga gtgtgcactg atccccaagc gtacaaggaa | 600 |
| tccaactata gctactgtct ctcatctcgg ctccgggtga gtgcgacatt ctggcataat | 660 |
| cctcggaacc actttcgatg ccaagtgcag tttcatgggt tgagcgagga agacaagtgg | 720 |
| cccgagggca gtcctaaacc agtcactcaa acataagcg ccgaggcatg gggtagagcc | 780 |
| gattgtggga ttactagcgc ttcataccaa caaggggtat tgagcgctac aattctttac | 840 |
| gaaattctcc tcggcaaggc gacgctctac gccgtactgg tgtctactct cgtggttatg | 900 |
| gcaatggtga aacggaaaaa cagcagagcc aaaagaagtg gttctggcgc gacgaatttt | 960 |
| agtttgctta agcaagccgg agatgtggag gaaaatcctg gaccgatgtg gggtgtcttc | 1020 |
| cttttgtacg tcagcatgaa gatgggaggc actactgggc aaaacataga tcagcctacc | 1080 |
| gaaatgactg ctaccgaggg agccattgtc caaatcaact gcacctatca gactagcggc | 1140 |
| ttcaatggac tcttctggta ccaacagcat gcgggcgaag cacctacctt cttgtcctat | 1200 |
| aatgtcttgg atggtctcga agagaaaggc agattctcca gtttcctcag ccggagcaag | 1260 |
| ggatactcat atcttctcct gaaagagctt cagatgaagg attctgcatc ctatctctgt | 1320 |

-continued

```
gcttcagtcg atggcaataa ccgactcgcc tttggaaaag ggaatcaagt ggtcgtcata   1380
ccgaatattc agaaccccga accagccgta tatcagttga aggacccaag atctcaggat   1440
agtacactct gtttgtttac ggactttgac tcacaaatca acgtcccgaa gactatggaa   1500
agtggtacgt tcatcacaga taagtgcgtt ctggacatga aggctatgga ctcaaagagc   1560 aacgggcaa  ttgcttggtc caaccagaca agctttacct gtcaggacat ttttaaggag   1620
actaatgcta cttatccctc cagcgacgtt ccgtgtgatg cgactcttac cgagaagtct   1680
tttgagaccg atatgaatct caacttccag aatctgctgg tgatcgttct gcggatcctg   1740
cttctgaagg ttgcaggatt caatcttctt atgactctcc ggctctggtc ttcatgataa   1800
```